United States Patent
DeLuca et al.

(10) Patent No.: US 7,528,122 B2
(45) Date of Patent: May 5, 2009

(54) VITAMIN D ANALOG—NEL, METHODS AND USES THEREOF

(75) Inventors: Hector F. DeLuca, Deerfield, WI (US); Grazia Chiellini, Madison, WI (US); Pawel Grzywacz, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 53 days.

(21) Appl. No.: 11/669,029

(22) Filed: Jan. 30, 2007

(65) Prior Publication Data

US 2007/0191316 A1    Aug. 16, 2007

Related U.S. Application Data

(60) Provisional application No. 60/743,217, filed on Feb. 2, 2006.

(51) Int. Cl.
*A61K 31/59* (2006.01)
*C07C 401/00* (2006.01)

(52) U.S. Cl. .................................. 514/167; 552/653
(58) Field of Classification Search .............. 552/653; 514/167
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | DeLuca et al. | |
| 5,585,369 A | 12/1996 | DeLuca et al. | |
| 5,843,928 A * | 12/1998 | Deluca et al. | 514/167 |
| 5,945,410 A | 8/1999 | DeLuca et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 6,887,860 B2 | 5/2005 | DeLuca et al. | |
| 6,894,037 B2 * | 5/2005 | DeLuca et al. | 514/167 |
| 6,939,868 B2 * | 9/2005 | DeLuca et al. | 514/167 |
| 6,992,074 B2 | 1/2006 | DeLuca et al. | |
| 7,053,075 B2 | 5/2006 | DeLuca et al. | |
| 7,235,680 B2 * | 6/2007 | DeLuca et al. | 552/653 |
| 7,241,749 B2 * | 7/2007 | DeLuca et al. | 514/167 |
| 2005/0070512 A1 | 3/2005 | Lee | |
| 2005/0119242 A1 | 6/2005 | DeLuca et al. | |
| 2007/0238702 A1 | 10/2007 | DeLuca et al. | |

FOREIGN PATENT DOCUMENTS

| | | |
|---|---|---|
| WO | 02/094247 | 11/2002 |
| WO | WO 03/082300 | 10/2003 |
| WO | 2004/080922 | 9/2004 |
| WO | 2005/018648 | 3/2005 |
| WO | 2005/051323 | 6/2005 |
| WO | WO 2006/119309 | 11/2006 |

OTHER PUBLICATIONS

Ostrem et al, "24- and 26-homo-1,25-dihydroxyvitamin $D_3$: Preferential activity in inducing differentiation of human leukemia cells HL-60 in vitro," Proc. Natl. Acad. Sci. USA, vol. 84, pp. 2610-2614, (1987).

Perlman et al, "1α,25-Dihydroxy-19-Nor-Vitamin $D_3$. A Novel Vitamin D-Related Compound with Potential Therapeutic Activity," Tetrahedron Letters, vol. 31 No. 13, pp. 1823-1824, (1990).

Perlman et al, "Novel Synthesis of 19-Nor-Vitamin D Compounds," Tetrahedron Letters, vol. 32 No. 52, pp. 7663-7666, (1991).

Okano et al, "Regulatory Activities of 2β-(3-Hydroxypropoxy)-1α,25-Dihydroxy-Vitamin $D_3$, a Novel Synthetic Vitamin $D_3$ Derivative, on Calcium Metabolism," Biochemical and Biophysical Research Communications, vol. 163 No. 3, pp. 1444-1449, (1989).

Miyamoto et al, "Synthetic Studies of Vitamin D Analogues. XIV. Synthesis and Calcium Regulating Activity of Vitamin $D_3$ Analogues Bearing a Hydroxyalkoxy Group at the 2β-Position," Chem. Pharm. Bull., vol. 41 No. 6, pp. 1111-1113, (1993).

Nishii et al, "The Development of Vitamin $D_3$ Analogues for the Treatment of Osteoporosis," Osteoporosis Int., Suppl. 1, pp. S190-193, (1993).

Posner et al, "Stereocontrolled Total Synthesis of Calcitriol Derivatives: 1,25-Dihydroxy-2-(4'-hydroxybutyl)vitamin $D_3$ Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin $D_3$. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Lythgoe et al, "Calciferol and its Relatives. Part22. A Direct Total Synthesis of Vitamin $D_2$ and Vitamin $D_3$," J. Chem. Soc. Perkin Trans. 1, p. 590, (1978).

Lythgoe, "Synthetic Approaches to Vitamin D and its Relatives," Chem. Soc. Rev. 9, p. 449, (1983).

Toh et al, "Studies on a Convergent Route to Side-Chain Analogues of Vitamin D: 25-Hydroxy-23-Oxavitamin $D_3$," J. Org. Chem., 48, 1414, (1983).

Baggiolini et al., "Stereocontrolled Total Synthesis of $1\alpha,25$-Dihydroxycholecalciferol and $1\alpha,25$-Dihydroxyergocalciferol," Journal of Organic Chemistry, 51, pp. 3098-3108, (1986).

Sardina et al, "Studies on the Synthesis of Side-Chain Hydroxylated Metabolites of Vitamin D. 2. Stereocontrolled Synthesis of 25-Hydroxyvitamin $D_2$," J. Org. Chem., 51, pp. 1264-1269, (1986).

Sicinski et al, "New $1\alpha,25$-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, (1998).

Mincione et al, "Improved Conversion of Vitamin $D_2$ into the Windaus Ketone and its Regioselective Hydroxylation via Organoboranes at $C_{26}$," Synthetic Communications, vol. 19 Nos. 5-6, pp. 723-735, (1989).

Peterson et al, "Studies of the Ketone Obtained from the Ozonolysis of Vitamin D. Molecular Mechanics Calculations for It and Related Hydrindanones," Journal of Organic Chemistry, vol. 51 No. 11, pp. 1948-1954 (1986).

Daniewski et al, "A Novel Silylcopper Catalyst for the Reductive Bromination of Hajos Dione. Improved Preparation of a CD Synthon for the Synthesis of Vitamin D," vol. 66 No. 2, pp. 626-628, (2001).

\* cited by examiner

*Primary Examiner*—Sabiha N. Qazi
(74) *Attorney, Agent, or Firm*—Andrus, Sceales, Starke & Sawall, LLP

(57) ABSTRACT

Compounds of formula IA or IB are provided where $X_1$, $X_2$ and $X_3$ are independently selected from H or hydroxy protecting groups and $R_1$ is selected from straight or branched chain alkyl groups having from 1 to 8 carbon atoms; straight or branched chain alkenyl groups having from 2 to 8 carbon atoms; straight or branched chain hydroxy-substituted alkyl groups having from 1 to 8 carbon atoms; straight and branched chain hydroxy-substituted alkenyl groups having from 2 to 8 carbon atoms. Such compounds are used in preparing pharmaceutical compositions and are useful in treating a variety of biological conditions.

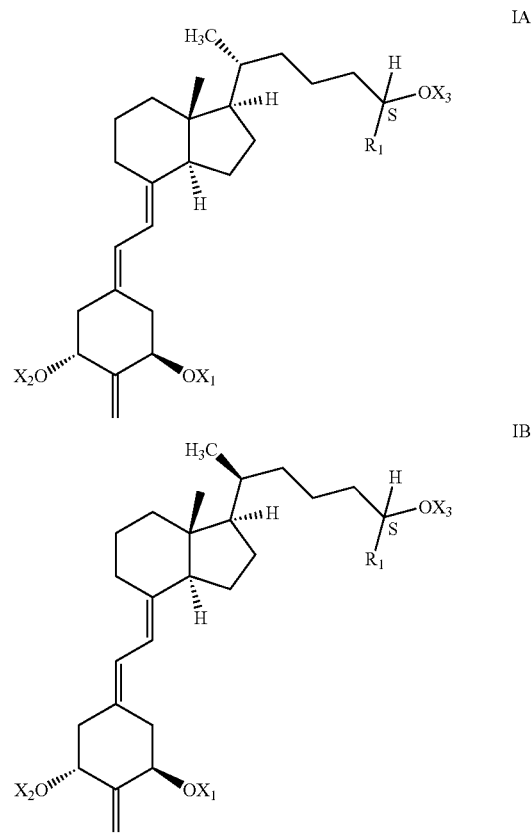

20 Claims, 5 Drawing Sheets

VITAMIN D ANALOG—NEL, METHODS AND USES THEREOF

This application seeks priority from U.S. provisional application 60/743,217 filed on Feb. 2, 2006, which is incorporated herein by reference, for all purposes.

FIELD OF THE INVENTION

This invention relates to vitamin D compounds, and more particularly to (20R, 25S)-2-Methylene-19,26-dinor-1α,25-dihydroxyvitamin D3 (NEL) and to pharmaceutical formulations that include this compound. The invention also relates to the use of (20R, 25S)-2-Methylene-19,26-dinor-1α,25-dihydroxyvitamin D3 or salts thereof in the preparation of medicaments for use in treating various diseases.

BACKGROUND OF THE INVENTION

The natural hormone, 1α,25-dihydroxyvitamin D3 (also referred to as 1α,25-dihydroxycholecalciferol and calcitriol) and its analog in the ergosterol series, i.e. 1α,25-dihydroxyvitamin D2 are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin D3, 1α-hydroxyvitamin D2, various side chain homologated vitamins, and fluorinated analogs. Some of these compounds exhibit an interesting separation of activities in cell differentiation and calcium regulation. This difference in activity is useful in the treatment of a variety of diseases as established in the art, such as renal osteodystrophy, vitamin D-resistant rickets, osteoporosis, psoriasis, and certain malignancies (see for example, Zemplar, Calcipotriol, MC-903, Dovonex, 22-oxa-1α, 25-(OH)2D3) Slatopolsky, E., Finch, J., Ritter, C., Denda, M., Morrissey, J., Brown, A. & DeLuca, H. (1995) Am. J. Kidney Dis. 26, 852-860; Kubodera, N., Sato, K. & Nishii, Y. (1997) in Vitamin D, eds. Feldman, D., Glorieux, F. H. & Pike, J. W. (Academic, New York), Vol. 63, pp. 1071-1086; Calverley, M. J. (1987) Tetrahedron Lett. 43, 4609-4619; Uskokovic, M. R., Studzinski, G. P. & Reddy, S. G. (1997) in Vitamin D, eds. Feldman, D., Glorieux, F. H. & Pike, J. W. (Academic, New York), Vol. 62, pp. 1045-1070; Kensler, T. W., Dolan, P. M., Gange, S. J., Lee, J.-K., Wang, Q. & Posner, G. H. (2000) Carcinogenesis 21, 1341-1345; Binderup, L., Binderup, E. & Godfredsen, W. O. (1997) in Vitamin D, eds. Feldman, D., Glorieux, F. H. & Pike, J. W. (Academic, New York), Vol. 61, pp. 1027-1043; Jones, G. (1997) in Vitamin D, eds. Feldman, D., Glorieux, F. H. & Pike, J. W. (Academic, New York), Vol. 58, pp. 973-994; Brown, A. J. & Slatopolsky, E. (1997) in Vitamin D, eds. Feldman, D., Glorieux, F. H. & Pike, J. W. (Academic, New York), Vol. 59, pp. 995-1009; Shankar, V. N., Propp, A. E., Schroeder, N. S., Surber, B. W., Makin, H. L. J. & Jones, G. (2001) Arch. Biochem. Biophys. 387, 297-306. All these references are incorporated herein by reference for al purposes.

Renal osteodystrophy is a bone disease that occurs when the kidneys fail to maintain the proper levels of calcium and phosphorus in the blood. Renal osteodystrophy is a common problem in people with kidney disease and affects 90 percent of dialysis patients.

Renal osteodystrophy is most serious in children because their bones are still growing. The condition slows bone growth and causes deformities. One such deformity occurs when the legs bend inward toward each other or outward away from each other; this deformity is referred to as "renal rickets." Another important consequence is short stature. Symptoms can be seen in growing children with renal disease even before they start dialysis.

The bone changes from renal osteodystrophy can begin many years before symptoms appear in adults with kidney disease. The symptoms of renal osteodystrophy are not usually seen in adults until they have been on dialysis for several years. Older patients and women who have gone through menopause are at greater risk for this disease because they're already vulnerable to osteoporosis, even without kidney disease. If left untreated, the bones gradually become thin and weak, and a person with renal osteodystrophy begins to experience bone and joint pain and an increased risk of bone fractures.

In healthy adults, bone tissue is continually being remodeled and rebuilt. The kidneys play an important role in maintaining healthy bone mass and structure because it balances calcium and phosphorus levels in the blood. If calcium levels in the blood become too low, the parathyroid glands release parathyroid hormone (PTH). This hormone draws calcium from the bones to raise blood calcium levels. Too much PTH in the blood causes disturbances in calcium and phosphorus homeostasis. This in turn removes too much calcium from the bones; over time, the constant removal of calcium weakens the bones.

Secondary hyperparathyroidism is characterized by an elevation of PTH associated with inadequate levels of active vitamin D hormone. Typically, Vitamin D requires two sequential hydroxylations in the liver and the kidney to bind and to activate the Vitamin D receptor (VDR). The endogenous VDR activator, calcitriol [$1,25(OH)_2D_3$] is a hormone that binds to VDR that is expressed in the parathyroid gland, intestine, kidney, and bone to maintain parathyroid function and calcium and phosphorus homeostasis, and to VDR found in many other tissues, including prostate, endothelium and immune cells. Phosphorus also helps regulate calcium levels in the bones. Healthy kidneys remove excess phosphorus from the blood. When the kidneys stop working normally, phosphorus levels in the blood can become too high, leading to lower levels of calcium in the blood and resulting in the loss of calcium from the bones.

Healthy kidneys produce calcitriol to help the body absorb dietary calcium into the blood and the bones. If calcitriol levels drop too low, PTH levels increase, and calcium is removed from the bones. Calcitriol and PTH work together to keep calcium balance normal and bones healthy. In a patient with kidney failure, the kidneys stop making calcitriol, dietary calcium is not absorbed and calcium is removed from the bones.

Controlling PTH levels prevents calcium from being withdrawn from the bones. Usually, overactive parathyroid glands are controllable with a change in diet, dialysis treatment, or medication. The drug cinacalcet hydrochloride (Sensipar), approved by the Food and Drug Administration in 2004, lowers PTH levels by binding to the calcium receptor that controls PTH release. If PTH levels cannot be controlled, the parathyroid glands may need to be removed surgically. Other treatments for the condition include taking synthetic calcitriol as a pill or in an injectable form.

Renal osteodystrophy can also be treated with changes in diet. Reducing dietary intake of phosphorus is one of the most important steps in preventing bone disease. Often, medications such as calcium carbonate (Tums), calcium acetate (PhosLo), sevelamer hydrochloride (Renagel), or lanthanum carbonate (Fosrenol) are prescribed with meals and snacks to bind phosphorus in the bowel, which decreases the absorption of phosphorus into the blood.

Other treatment choices for renal osteodystrophy include Paricalcitol, the active ingredient of Zemplar (paracalcitol injection, USP), which is a synthetic, biologically active vitamin D analog of calcitriol with modifications to the side chain and the A (19-nor) ring. Preclinical and in vitro studies have demonstrated that paricalcitol's actions are mediated through binding to the VDR, resulting in the selective activation of Vitamin D response pathways. Calcitriol and paricalcitol have been shown to reduce parathyroid hormone levels by inhibiting PTH synthesis and secretion.

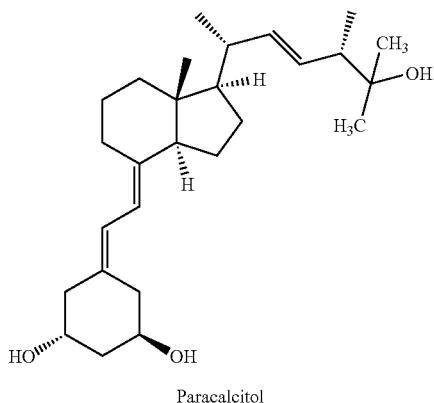

Paracalcitol

The structure of 1α,25-dihydroxyvitamin $D_3$ and the numbering system used to denote the carbon atoms in this compound are shown below.

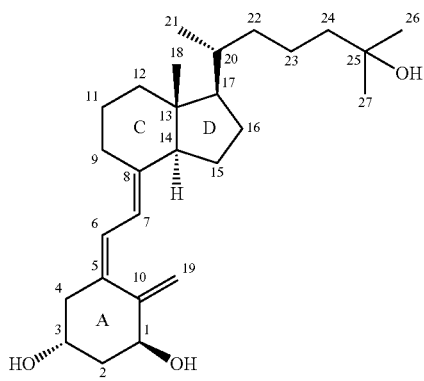

1α,25-Dihydroxyvitamin $D_3$ = 1α, 25-Dihydroxycholecalciferol = Calcitriol

Typically, the class of vitamin D analogs such as 19-nor-vitamin D compounds is characterized by the absence of carbon 19 from the A-ring exocyclic methylene group, typical of the vitamin D system. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., *Tetrahedron Lett.* 31, 1823 (1990);

Perlman et al., *Tetrahedron Lett.* 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by the Chugai group as potential drugs for osteoporosis and as antitumor agents. See also Okano et al., *Biochem. Biophys. Res. Commun.* 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al, *Chem. Pharm. Bull.* 41, 1111 (1993); Nishii et al., *Osteoporosis Int. Suppl.* 1, 190 (1993); Posner et al., *J. Org. Chem.* 59, 7855 (1994), and *J. Org. Chem.* 60, 4617 (1995)).

Various 2-substituted analogs of 1α,25-dihydroxy-19-nor-vitamin $D_3$ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs that are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents. Other 19-nor compounds are disclosed in U.S. patent application Ser. Nos. 10/996,642 and 10/997,698. All these patents and patent applications are incorporated herein by reference for all purposes.

Since the currently available treatments, including compounds and formulations described above have various limitations to a greater or lesser extent, new compounds and pharmaceutical formulations are desirable that continue to decrease the calcemic effect while retaining the ability to suppress PTH.

SUMMARY OF THE INVENTION

The invention generally provides (20R, 25S)-2-Methylene-19,26-dinor-1α,25-dihydroxyvitamin D3 (NEL)and related compounds, pharmaceutical formulations that include NEL and the use of this compound in the preparation of medicaments for use in treating various disease states.

Therefore, in one aspect, the invention provides a compound having the formula IA or IB as shown below:

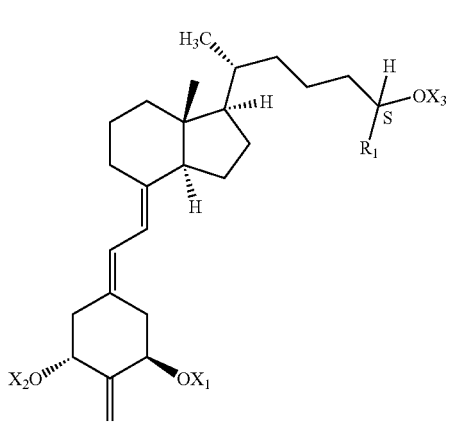

IA

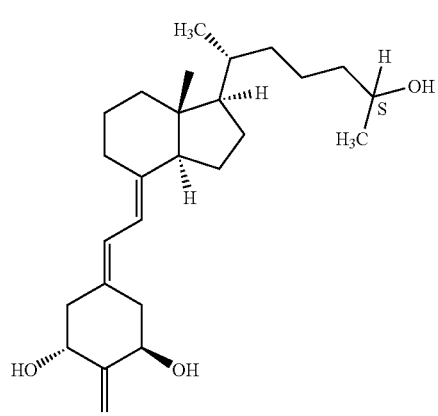

II A

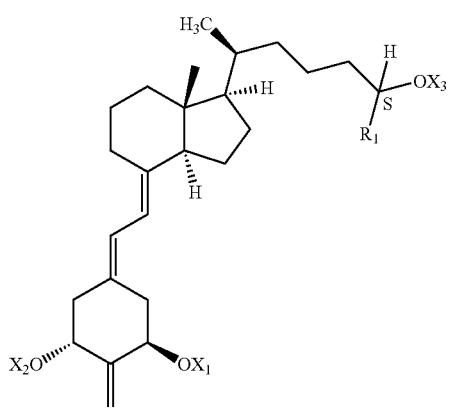

IB

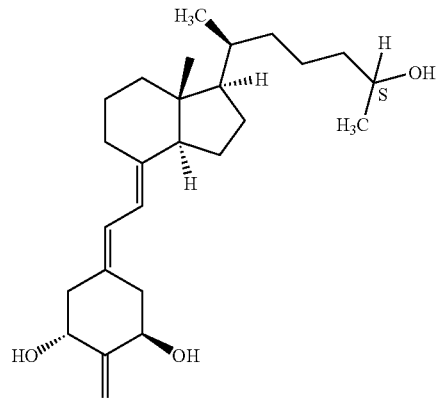

II B where $X_1$, $X_2$ and $X_3$ is the same or different and are independently selected from H or hydroxy-protecting groups. In some embodiments, $X_1$, $X_2$ and $X_3$ are hydroxy protecting groups such as silyl groups. In some such embodiments, $X_1$, $X_2$ and $X_3$ are t-butyldimethylsilyl groups. In certain embodiments, $R_1$ is selected from straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. In some such embodiments, $R_1$ is selected from straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R_1$ is selected from straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms.

In other embodiments, $X_1$, $X_2$ and $X_3$ are H and $R_1$ is $CH_3$ such that the compound is (20R, 25S)-2-Methylene-19,26-dinor-1α,25-dihydroxyvitamin D3 having the formula IIA or (20S, 25S)-2-Methylene-19,26-dinor-1α,25-dihydroxyvitamin D3 having the formula II B as shown below:

Another embodiment of the present invention provides a pharmaceutical composition, comprising an effective amount of the compound of formula IA or IB and a pharmaceutically acceptable carrier. In this pharmaceutical composition, the effective amount comprises from about 0.01 μg to about 1 mg of the compound per gram of the composition. More preferably, the effective amount comprises from about 0.1 μg to about 500 μg of the compound per gram of the composition.

In certain embodiments, the present invention provides a method of treating a subject suffering from a biological condition, comprising administering an effective amount of the compound of formula IA or IB to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis. In a preferred embodiment, the biological condition is renal osteodystrophy, vitamin D-resistant rickets, osteoporosis or psoriatic arthritis. In another preferred embodiment, the biological condition is selected from leukemia, colon cancer, breast cancer, or prostate cancer. In yet another preferred embodiment, the biological condition is selected from multiple sclerosis, lupus, diabetes mellitus, host versus graft reaction, or rejection of organ transplants. In still other preferred embodiment, the biological condition is selected from rheumatoid arthritis, asthma, or inflammatory bowel diseases selected from celiac disease, ulcerative colitis and Crohn's disease. In yet other preferred embodiment, the biological condition is selected from wrinkles, lack of adequate skin firmness, lack of adequate dermal hydration, or insufficient sebum secretion.

Also preferably, in this embodiment, the effective amount of the compound is administered orally, parenterally, transdermally or topically to the subject. Yet more preferably, the effective amount of the compound is administered intraperitoneally. In this embodiment, the compound is administered in a dosage of from 0.01 μg per day to 1 mg per day.

Another aspect of the invention provides the use of the compound of formula IA or IB in the preparation of a medicament for the treatment of a biological condition selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

Yet another preferred embodiment of the present invention provides the compound having the formula IIA

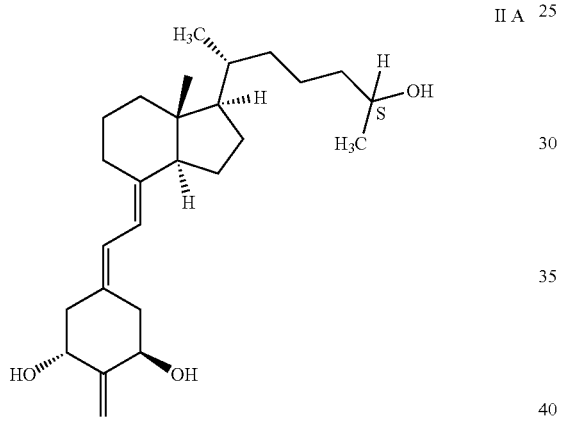

The invention also teaches a pharmaceutical composition having an effective amount of the compound of formula IIA and a pharmaceutically acceptable carrier.

Another aspect of the invention provides the use of the compound of formula IIA in the preparation of a medicament for the treatment of a biological condition selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

Further objects, features and advantages of the invention will be apparent from the following detailed description, drawings and appended claims.

BRIEF DESCRIPTION OF THE DRAWINGS

FIG. 1 is a graph comparing the relative activity of NEL and 1,25(OH)$_2$D$_3$ to compete for binding with [$^3$H]-1,25-(OH)$_2$-D$_3$ to the full-length recombinant rat vitamin D receptor.

FIG. 2 is a bar graph comparing the bone calcium mobilization activity of NEL with that of 1,25(OH)$_2$D$_3$.

FIG. 3 is a bar graph comparing the intestinal calcium transport activity of NEL with that of 1,25(OH)$_2$D$_3$.

FIG. 4 is a graph comparing the percent HL-60 cell differentiation as a function of the concentration of NEL with that of 1,25(OH)$_2$D$_3$.

FIG. 5 is a graph comparing the in vitro transcription activity of NEL with that of 1,25(OH)$_2$D$_3$.

DETAILED DESCRIPTION OF THE INVENTION

Figure 1:
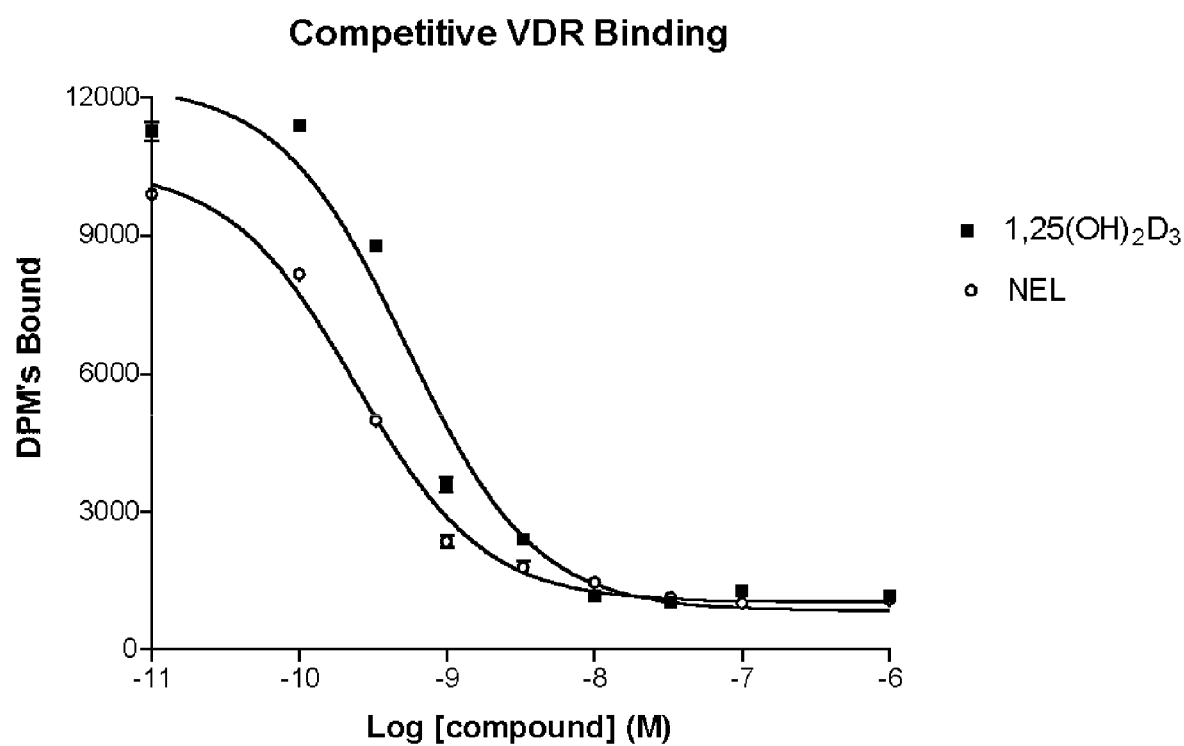
FIGS. 1-5 illustrate various biological activities of (20R, 25S)-2-Methylene-19,26-dinor-1α,25-dihydroxyvitamin D3 (referred to as "NEL" in the Figures) compared with those of the native hormone 1α, 25-dihydroxyvitamin $D_3$ (referred to as "1, 25(OH)$_2$D$_3$" in the Figures).

Generally, the invention provides a compound having the formula IA or IB as shown below:

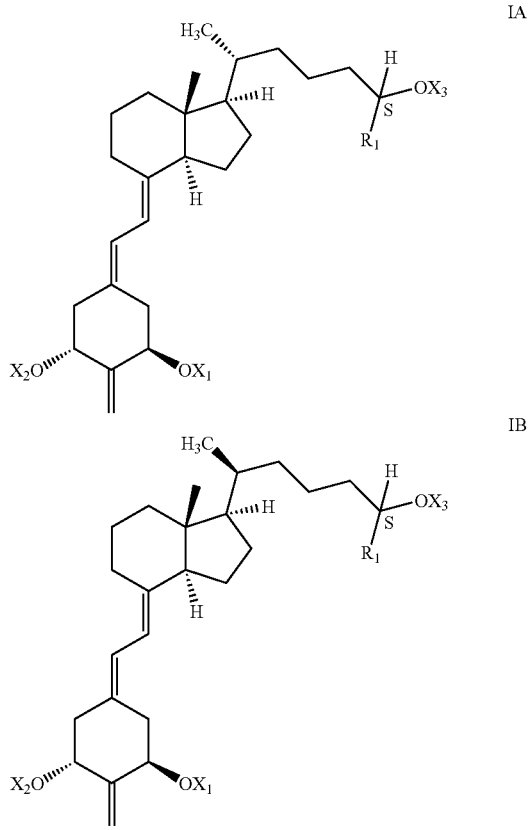

where $X_1$, $X_2$ and $X_3$ is the same or different and are independently selected from H or hydroxy-protecting groups. In some embodiments, $X_1$, $X_2$ and $X_3$ are hydroxy protecting groups such as silyl groups. In some such embodiments, $X_1$, $X_2$ and $X_3$ are t-butyldimethylsilyl groups. In certain embodiments, $R_1$ is selected from straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. In some such embodiments, $R_1$ is selected from straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R_1$ is selected from straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms.

As used herein, the phrase "straight and branched chain alkyl groups" refers to groups that include carbon and hydrogen atoms that only include carbon-carbon single bonds and carbon-hydrogen single bonds. These groups do not include any heteroatoms (atoms other than H or C). Thus, the phrase "straight and branched chain alkyl groups" includes straight chain alkyl groups such as methyl, ethyl, propyl, butyl, pentyl, hexyl, heptyl, and octyl groups and branched chain isomers of straight chain alkyl groups, including but not limited to, the following which are provided by way of example only:
—CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH$_2$CH$_2$CH$_2$C(CH$_3$)$_3$, —CH$_2$CH$_2$CH$_2$CH(CH$_3$)$_2$, —CH$_2$CH$_2$CH(CH$_3$)C(CH$_3$)$_3$, —CH$_2$CH$_2$CH(CH$_3$)CH(CH$_3$)$_2$, and the like.

As used herein, the phrase "hydroxy-substituted alkyl groups" refers to "straight and branched chain alkyl groups" as defined above in which a bond to a carbon or a hydrogen atom is replaced by a bond to a hydroxyl (—OH) group.

As used herein, the phrase "straight and branched chain alkenyl groups" refers to "straight and branched chain alkyl groups" as defined above, except that at least one double bond exists between two of the carbon atoms. Examples include, but are not limited to the cis and trans (Z and E) isomers of —CH═CH$_2$, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, —C(H)═C(H)CH$_2$CH(CH$_3$)$_2$, —C(H)═C(H)CH(CH$_3$)CH(CH$_3$)$_2$, —C(H)═C(H)CH$_2$C(CH$_3$)$_3$, —C(H)═C(H)CH(CH$_3$)C(CH$_3$)$_3$, and the like.

As used herein, the phrase "hydroxy-substituted alkenyl groups" has the same meaning with respect to "straight and branched chain alkenyl groups" that "hydroxy-substituted alkyl groups" had with respect to "straight and branched chain alkyl groups". Therefore, "hydroxy-substituted alkenyl groups" are "straight and branched chain alkenyl groups" in which a bond to a hydrogen atom or carbon atom that is not double-bonded to another carbon atom is replaced by a bond to a hydroxyl (—OH) group.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality is found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

In other embodiments, $X_1$, $X_2$ and $X_3$ are H and $R_1$ is $CH_3$ such that the compound is (20R, 25S)-2-Methylene-19,26-dinor-1α,25-dihydroxyvitamin D3 having the formula IIA or (20S, 25S)-2-Methylene-19,26-dinor-1α,25-dihydroxyvitamin D3 having the formula II B as shown below:

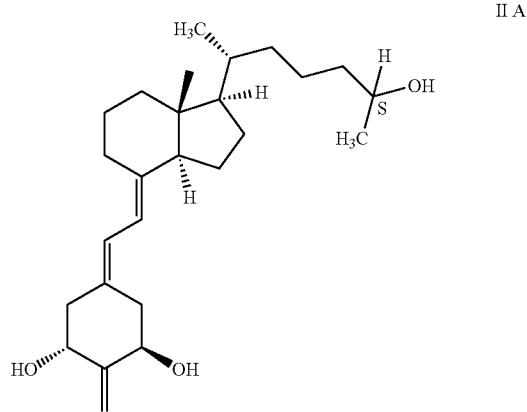

II A

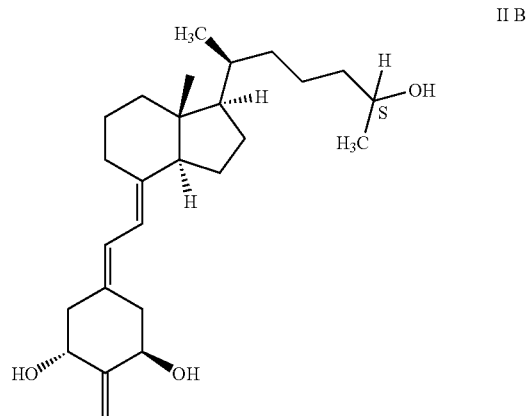

II B

The compound of formula IIA (NEL) exhibits a desired, and highly advantageous, pattern of biological activity. This compound is characterized by relatively high binding to vitamin D receptors, but very low intestinal calcium transport activity, as compared to that of 1α,25-dihydroxyvitamin $D_3$, and has very low ability to mobilize calcium from bone, as compared to 1,25-dihydroxyvitamin $D_3$. Hence, this compound can be characterized as having little, if any, calcemic activity. Thus, it is useful as a therapy for suppression of secondary hyperparathyroidism or renal osteodystrophy.

The compound of the invention is also especially suited for treatment and prophylaxis of human disorders which are characterized by an imbalance in the immune system, e.g. in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which are treated with the compound of the invention.

The above compound is also characterized by relatively high cell differentiation activity. Thus, this compound also provides a therapeutic agent for the treatment of psoriasis, or as an anti-cancer agent, especially against leukemia, colon cancer, breast cancer and prostate cancer. In addition, due to its relatively high cell differentiation activity, this compound provides a therapeutic and/or cosmetic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compounds of the invention are used to prepare pharmaceutical formulations or medicaments that include a compound of the invention in combination with a pharmaceutically acceptable carrier. Such pharmaceutical formulations and medicaments are used to treat various biological disorders such as those described herein. Methods for treating such disorders typically include administering an effective amount of the compound or an appropriate amount of a pharmaceutical formulation or a medicament that includes the compound to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compounds is present in a composition to treat the above-noted diseases and disorders in an amount from about 0.01 μg/gm to about 1 mg/gm of the composition, preferably from about 0.1 μg/gm to about 500 μg/gm of the composition, and is administered topically, transdermally, orally, or parenterally in dosages of from about 0.01 μg/day to about 1 mg/day, preferably from about 0.1 μg/day to about 500 μg/day.

In one embodiment, the compounds IA or IB are compounds IIA or IIB as shown below:

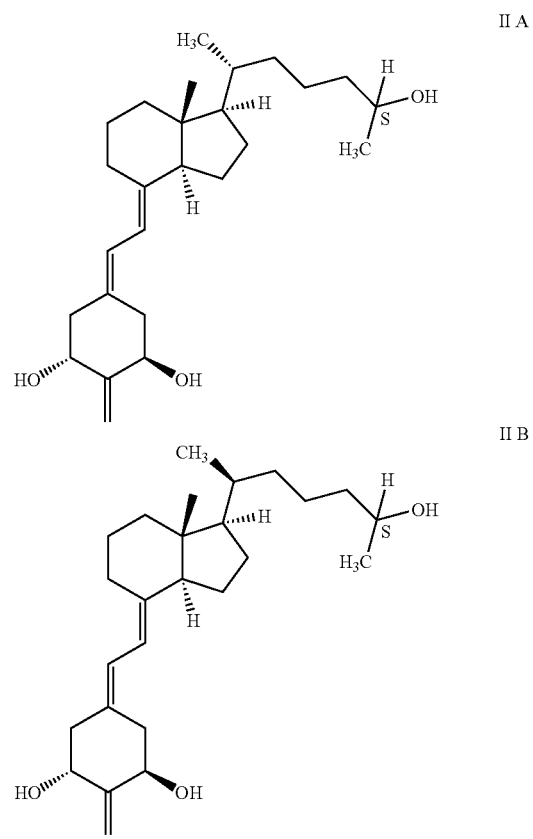

In a preferred embodiment, (20R, 25S)-2-Methylene-19, 26-dinor-1α,25-dihydroxyvitamin D3 (NEL) was synthesized, and tested, and is useful in treating a variety of biological conditions as described herein.

Preparation of (20R, 25S)-2-Methylene-19,26-dinor-1α, 25-dihydroxyvitamin D3 can be accomplished by condensing an appropriate bicyclic Windaus-Grundmann type ketone (III) with the allylic phosphine oxide IV followed by deprotection (removal of the $Y_1$ and $Y_2$ groups). Other compounds of the present invention are similarly synthesized.

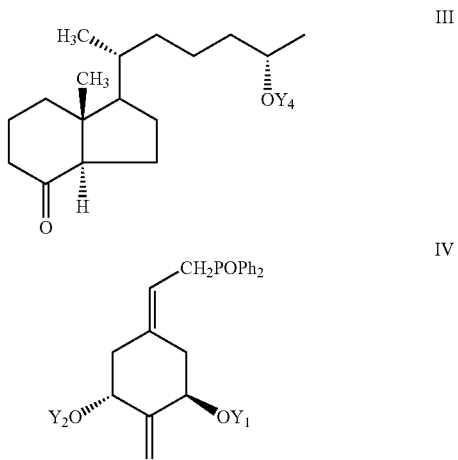

In ketone III, $Y_4$ is preferably a hydroxy-protecting group such as silyl protecting groups. The t-butyldimethylsilyl (TBDMS) group is an example of a particularly useful hydroxy-protecting group. In phosphine oxide IV, $Y_1$ and $Y_2$ are preferably hydroxy-protecting groups such as silyl protecting groups. The t-butyldimethylsilyl (TBDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I*, 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Phosphine oxide IV is a convenient reagent that can be used to prepare a large number of 19-nor vitamin D compounds and is prepared according to the procedures described by Sicinski et al., *J. Med. Chem.*, 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme I shows the general procedure for synthesizing phosphine oxide IV as outlined in U.S. Pat. No. 5,843,928 which is hereby incorporated by reference in its entirety as if fully set forth herein. Modification of the method shown in Scheme I is used to produce a large number of vitamin D analogs as will be apparent to those skilled in the art. For example, a wide variety of phosphonium compounds is used in place of the $MePh_3P^+Br^-$ used to convert ketone B to alkene C. Examples of such compounds include $EtPh_3P^+Br^-$, $PrPh_3P^+Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I is reduced with $(Ph_3P)_3RhCl$ and $H_2$ to provide other vitamin D analogs. See U.S. Pat. No. 5,945,410 and Sicinski, R. R. et al., *J. Med. Chem.*, 41, 4662-4674 (1998) both of which are hereby incorporated by reference in their entireties and for all purposes. Therefore, the procedure for forming the phosphine oxide shown in Scheme I is used to prepare a wide variety of vitamin D analogs in addition to the compound of the present invention.

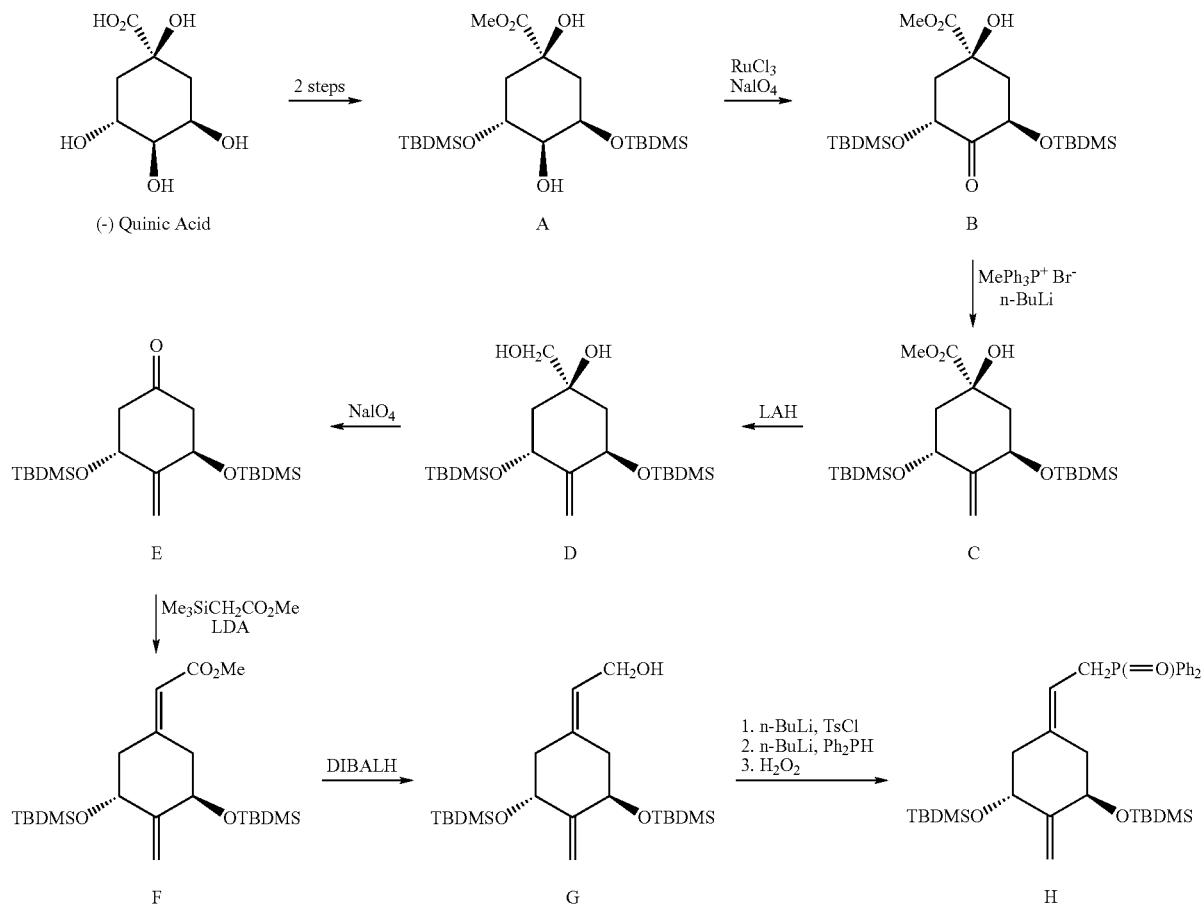

Scheme I

Hydraindanones of structure III can prepared by known methods or adapted methods as will be readily apparent to one of skill in the art and described herein. Specific examples of some important bicyclic ketones used to synthesize vitamin D analogs are those described in Mincione et al., *Synth. Commun* 19, 723, (1989); and Peterson et al., *J. Org. Chem.* 51, 1948, (1986).

In one preferred embodiment, ketone III having Y$_4$=TBSO (12) group is synthesized by the Schemes II and III, as shown below:

An overall process for synthesizing 2-alkylidene-19-nor-vitamin D compounds is illustrated and described in U.S. Pat. Nos. 5,843,928, 6,627,622, 6,579,861, 5,086,191, 5,585,369, and 6,537,981, which are hereby incorporated by reference in its entirety and for all purposes as if fully set forth herein.

In one preferred embodiment, compound of Formula IIA (NEL) was prepared by the following Scheme III:

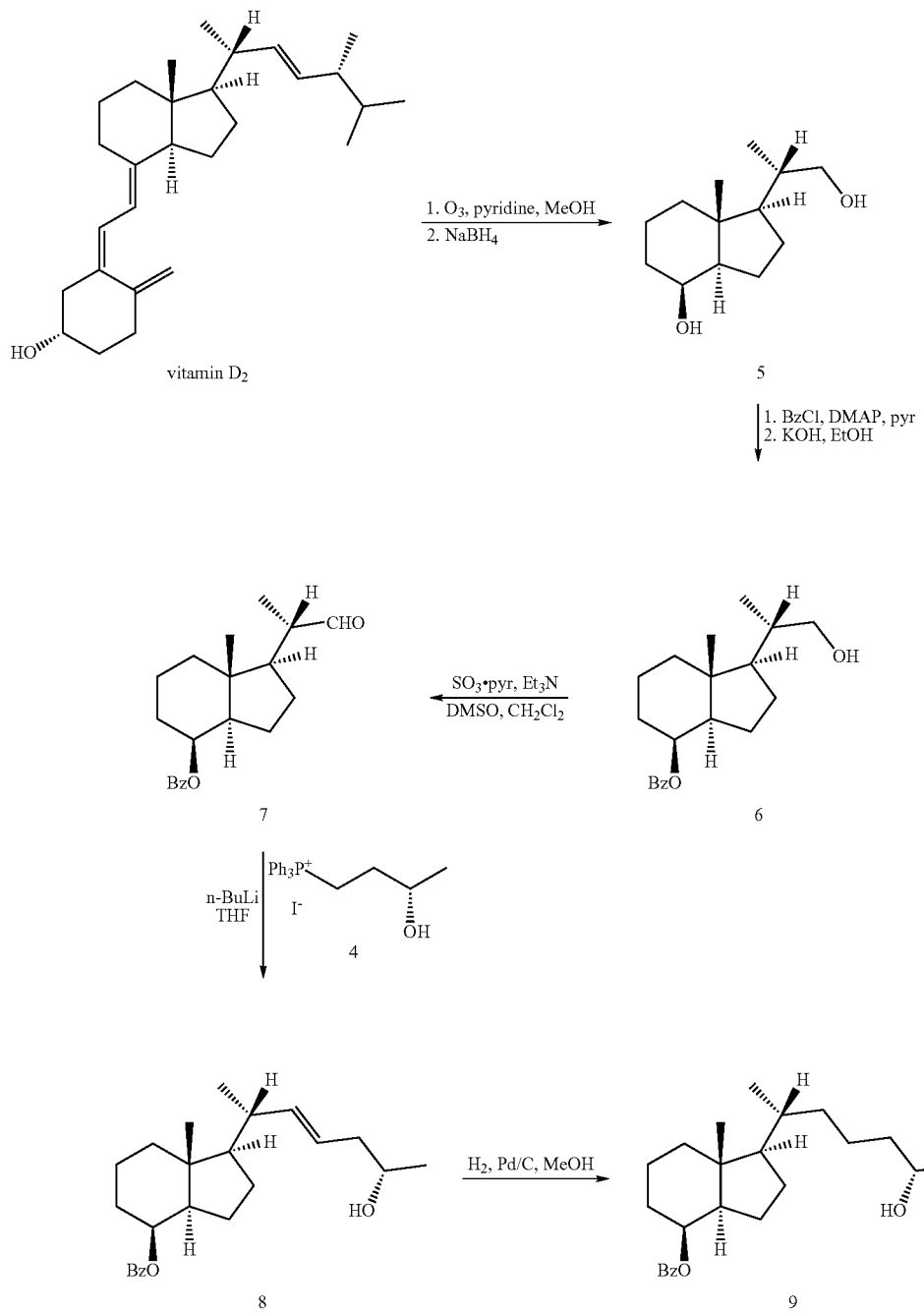

Scheme III
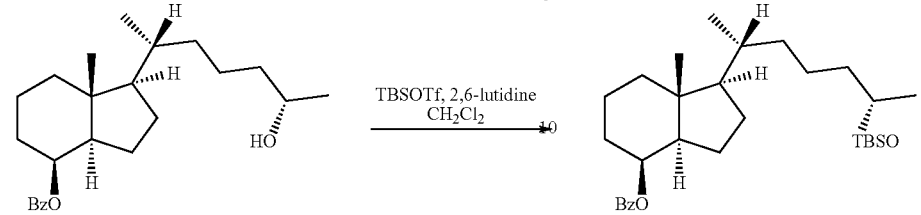
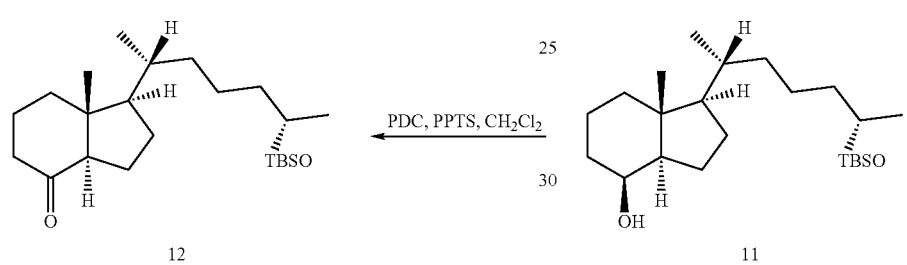
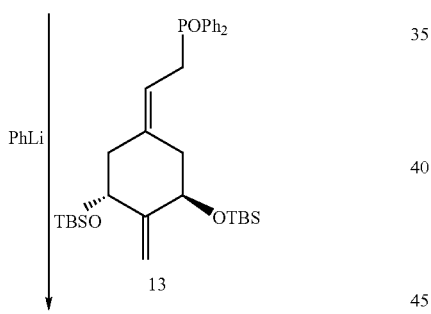
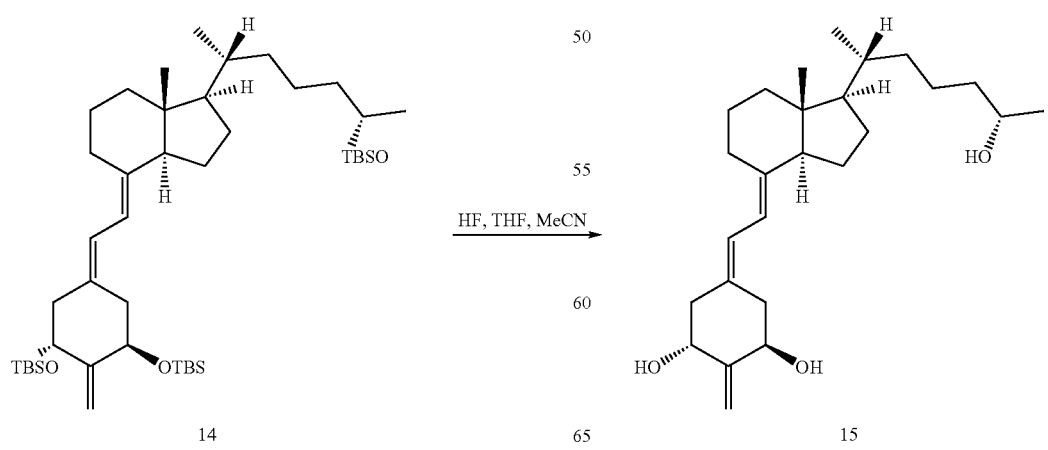

Compounds of formula I, formula IA, and formula IB and formula II, formula IIA and formula IIB can be prepared using the methods shown in Schemes I, II and III. For the compound of formula IIA, the starting material, compound 4, was prepared using known procedures, as shown below in Scheme IV. See also, Andrzej R. Daniewski and Wen Liu (*J. Org. Chem.* 66, 626-628 (2001), which is hereby incorporated by reference in its entirety and for all purposes as if fully set forth herein.

Scheme IV

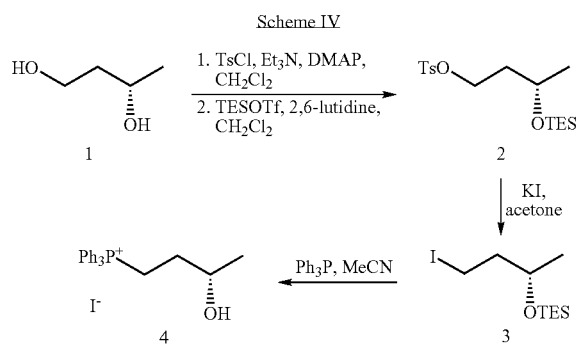

Following examples illustrate synthesis and biological activity of the compounds provided in the present invention. These Examples are for illustration purposes only and should not be deemed to limit the scope of the invention.

EXAMPLE I

NEL SYNTHESIS

Preparation of (3S)-1-p-Toluenesulfonyloxy-3-triethylsilyloxy-butane (2)

To a stirred solution of the (S)-(+)-1,3-butanediol 1 (1 g, 11.1 mmol), DMAP (30 mg, 0.25 mmol) and Et$_3$N (4.6 mL, 3.33 g, 33 mmol) in anhydrous methylene chloride (20 mL) p-toluenesulfonyl chloride (2.54 g, 13.3 mmol) was added at 0° C. The reaction mixture was stirred at 4° C. for 22 h. Methylene chloride was added and the mixture was washed with water, dried (Na$_2$SO$_4$) and concentrated under reduced pressure. A residue was chromatographed on silica gel with hexane/ethyl acetate (8:2, then 1:1) to afford the tosylate (2.31 g, 85% yield) as colorless oil.

To a stirred solution of the tosylate (2.31 g, 9.5 mmol) and 2,6-lutidine (1.2 mL, 1.12 g, 10.5 mmol) in anhydrous methylene chloride (15 mL) triethylsilyl trifluoromethanesulfonate (2.1 mL, 2.51 g, 9.5 mmol) was added at −50° C. The reaction mixture was allowed to warm to room temperature (4 h) and stirring was continued for additional 20 h. Methylene chloride was added and the mixture was washed with water, dried (Na$_2$SO$_4$) and concentrated under reduced pressure. A residue was chromatographed on silica gel with hexane/ethyl acetate (97:3) to afford the product 2 (2.71 g, 80% yield) as a colorless oil:

[α]$_D$ +18.0 (c 2.38, CHCl$_3$); $^1$H NMR (400 MHz, CDCl$_3$) δ 7.77 (2H, d, J=8.2 Hz, o-H$_{Ts}$), 7.33 (2H, d, J=8.2 Hz, m-H$_{Ts}$), 4.10 (2H, t, J=6.1 Hz, 1-H$_2$), 3.90 (1H, m, 3-H), 2.43 (3H, s, Me$_{Ts}$), 1.72 (2H, m, 2-H$_2$), 1.10 (3H, d, J=6.2 Hz, 4-H$_3$), 0.88 (9H, t, J=8.0 Hz, 3×SiCH$_2$CH$_3$), 0.50 (6H, q, J=8.0 Hz, 3×SiCH$_2$CH$_3$); $^{13}$C NMR (100 MHz) δ 144.62 (s, p-C$_{Ts}$), 133.03 (s, i-C$_{Ts}$), 129.72 (d, m-C$_{Ts}$), 127.82 (d, o-C$_{Ts}$), 67.78 (t, C-1), 64.46 (d, C-3), 38.47 (t, C-2), 23.82 (q, C-4), 21.52 (q, Me$_{Ts}$), 6.71 (q, SiCH$_2$CH$_3$), 4.77 (t, SiCH$_2$CH$_3$); MS (EI) m/z 359 (5, MH$^+$), 329 (87, M$^+$—C$_2$H$_5$), 259 (100), 233 (54), 197 (50), 179 (74), 163 (40), 149 (48), 135 (38), 115 (53), 91 (71); exact mass calculated for C$_{15}$H$_{25}$O$_4$SSi (M$^+$—C$_2$H$_5$), 329.1243. Found 329.1239.

Preparation of (3S)-1-Iodo-3-triethylsilyloxy-butane (3)

To a stirred solution of the tosylate 2 (2.71 g, 7.6 mmol) in anhydrous acetone (50 mL) potassium iodide (8 g, 48 mmol) was added and the reaction mixture was refluxed for 10 h. Water (30 mL) was added and the solution was extracted with ethyl acetate. The combined organic phases were dried (Na$_2$SO$_4$) and concentrated under reduced pressure. The residue was chromatographed on silica gel with hexane/ethyl acetate (97:3) to give the alcohol 3 (2.26 g, 95% yield) as a colorless oil:

[α]$_D$ +36.3 (c 2.12, CHCl$_3$); $^1$H NMR (400 MHz, CDCl$_3$) δ 3.89 (1H, m, 3-H), 3.22 (2H, t, J=7.0 Hz, 1-H$_2$), 1.91 (2H, m, 2-H$_2$), 1.16 (3H, d, J=6.1 Hz, 4-H$_3$), 0.96 (9H, t, J=7.9 Hz, 3×SiCH$_2$CH$_3$), 0.61 (6H, q, J=7.9 Hz, 3×SiCH$_2$CH$_3$); $^{13}$C NMR (100 MHz) δ 68.13 (d, C-3), 43.23 (d, C-2), 23.45 (q, C-4), 6.86 (q, SiCH$_2$CH$_3$), 4.99 (t, SiCH$_2$CH$_3$), 3.34 (t, C-1); MS (EI) m/z 314 (1, M$^+$), 299 (1, M$^+$—CH$_3$), 285 (100, M$^+$—C$_2$H$_5$), 257 (97, M$^+$—C$_4$H$_9$), 228 (51), 212 (98), 184 (58), 157 (62), 129 (33), 115 (31); exact mass calculated for C$_8$H$_{18}$OISi (M$^+$—C$_2$H$_5$) 285.0172. Found 285.0169.

Preparation of (3S)-Hydroxybutyl-triphenylphosphonium iodide (4)

To a stirred solution of the iodide 3 (1.67 g, 5.3 mmol) in acetonitrile (50 mL) triphenylphosphine (4.2 g, 16 mmol) was added and the reaction mixture was refluxed for 2 days. Acetonitrile was evaporated under reduced pressure, ethyl acetate (50 mL) was added and the mixture was stirred at room temperature for 4 h. After removal of the solvent by filtration the solid was washed with ethyl acetate, filtered off and dried. The pure phosphonium salt 4 (1.77 g, 87% yield) was obtained as white crystals:

$^1$H NMR (400 MHz, CD$_3$OD) δ 8.00-7.70 (15H, m, H$_{Ph}$), 3.89 (1H, m, 3-H), 3.48 (2H, m, 1-H$_2$), 1.73 (2H, m, 2-H$_2$), 1.19 (3H, d, J=6.2 Hz, 4-H$_3$); $^{13}$C NMR (100 MHz) δ 136.42 (d, p-C$_{Ph}$), 134.99 (d, J$_{C-P}$=10.1 Hz, m-C$_{Ph}$), 131.71 (d, J$_{C-P}$=13.1 Hz, o-C$_{Ph}$), 120.04 (s, J$_{C-P}$=86.5 Hz, i-C$_{Ph}$), 67.94 (d, J$_{C-P}$=16.2 Hz, C-3), 32.52 (t, J$_{C-P}$=4.1 Hz, C-2), 23.38 (q, C-4), 19.84 (t, J$_{C-P}$=53.7 Hz, C-1);

Preparation of (8S,20S)-de-A,B-20-(hydroxymethyl) pregnan-8-ol (5)

Ozone was passed through a solution of vitamin D2 (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with NaBH$_4$ (0.75 g, 20 mmol). After 20 min the second portion of NaBH$_4$ (0.75 g, 20 mmol) was added and the mixture was allowed to warm to room temperature. The third portion of NaBH$_4$ (0.75 g, 20 mmol) was then added and the reaction mixture was stirred for 18 h. The reaction was quenched with water (40 mL) and the solution was concentrated under reduced pressure. The residue was extracted with ethyl acetate and the combined organic phases were washed with 1M aq. HCl, saturated aq. NaHCO$_3$, dried (Na$_2$SO$_4$) and concentrated under reduced pressure. The residue was chromatographed on silica gel with hexane/ethyl acetate (75:25) to give the diol 5 (1.21 g, 75% yield) as white crystals:

m.p. 106-108° C.; $[\alpha]_D$+30.2° (c 1.46, CHCl$_3$); $^1$H NMR (400 MHz, CDCl$_3$) δ 4.08 (1H, d, J=2.0 Hz, 8 α-H), 3.63 (1H, dd, J=10.5, 3.1 Hz, 22-H), 3.38 (1H, dd, J=10.5, 6.8 Hz, 22-H), 1.99 (1H, br.d, J=13.2 Hz), 1.03 (3H, d, J=6.6 Hz, 21-H$_3$), 0.956 (3H, s, 18-H$_3$); $^{13}$C NMR (100 MHz) δ 69.16 (d, C-8), 67.74 (t, C-22), 52.90 (d), 52.33 (d), 41.83 (s, C-13), 40.19 (t), 38.20 (d), 33.53 (t), 26.62 (t), 22.54 (t), 17.36 (t), 16.59 (q, C-21), 13.54 (q, C-18); MS (EI) m/z 212 (2, M$^+$), 194 (34, M$^+$ —H$_2$O), 179 (33, M$^-$—H$_2$O—CH$_3$), 163 (18, M$^+$ —CH$_2$OH—H$_2$O), 135(36), 125 (54), 111 (100), 95 (63), 81 (67); exact mass calculated for C$_{13}$H$_{22}$O (M$^+$ —H$_2$O) 194.1671. Found 194.1665.

Preparation of (8S,20S)-de-A,B-8-benzoyloxy-20-(hydroxymethyl)pregnane (6)

Benzoyl chloride (2.4 g, 2 mL, 17 mmol) was added to a solution of the diol 5 (1.2 g, 5.7 mmol) and DMAP (30 mg, 0.2 mmol) in anhydrous pyridine (20 mL) at 0° C. The reaction mixture was stirred at 4° C. for 24 h, diluted with methylene chloride (100 mL), washed with 5% aq. HCl, water, saturated aq. NaHCO$_3$, dried (Na$_2$SO$_4$) and concentrated under reduced pressure. The residue (3.39 g) was treated with a solution of KOH (1 g, 15.5 mmol) in anhydrous ethanol (30 mL) at room temperature. After stirring of the reaction mixture for 3 h, ice and 5% aq. HCl were added until pH=6. The solution was extracted with ethyl acetate (3×50 mL) and the combined organic phases were washed with saturated aq. NaHCO$_3$, dried (Na$_2$SO$_4$) and concentrated under reduced pressure. The residue was chromatographed on silica gel with hexane/ethyl acetate (75:25) to give the alcohol 6 (1.67 g, 93% yield) as a colorless oil:

$[\alpha]_D$+56.0 (c 0.48, CHCl$_3$); $^1$H NMR (400 MHz, CDCl$_3$+TMS) δ 8.08-8.02 (2H, m, o-H$_{Bz}$), 7.59-7.53 (1H, m, p-H$_{Bz}$), 7.50-7.40 (2H, m, m-H$_{Bz}$), 5.42 (1H, d, J=2.4 Hz, 8 α-H), 3.65 (1H, dd, J=10.5, 3.2 Hz, 22-H), 3.39 (1H, dd, J=10.5, 6.8 Hz, 22-H), 1.08 (3H, d, J=5.3 Hz, 21-H$_3$), 1.07 (3H, s, 18-H$_3$); $^{13}$C NMR (125 MHz) δ 166.70 (s, C=O), 132.93 (d, p-C$_{Bz}$), 131.04 (s, i-C$_{Bz}$), 129.75 (d, o-C$_{Bz}$), 128.57 (d, m-C$_{Bz}$), 72.27 (d, C-8), 67.95 (t, C-22), 52.96 (d), 51.60 (d), 42.15 (s, C-13), 39.98 (t), 38.61 (d), 30.73 (t), 26.81 (t), 22.91 (t), 18.20 (t), 16 87 (q, C-21), 13.81 (q, C-18); MS (EI) m/z 316 (5, M$^+$), 301 (3, M$^+$-Me), 299 (1, M$^+$ —OH), 298 (2, M$^+$—H$_2$O), 285 (10, M$^+$ —CH$_2$OH), 257 (6), 230 (9), 194 (80), 135 (84), 105 (100); exact mass calculated for C$_{20}$H$_{28}$O$_3$ 316.2038. Found 316.2019.

Preparation of (8S,20S)-de-A,B-8-benzoyloxy-20-formylpregnane (7)

Sulfur trioxide pyridine complex (1.94 g, 12.2 mmol) was added to a solution of the alcohol 6 (640 mg, 2.03 mmol), triethylamine (1.41 mL, 1.02 g, 10.1 mmol) in anhydrous methylene chloride (10 mL) and anhydrous DMSO (2 mL) at 0° C. The reaction mixture was stirred under argon at 0° C. for 1 h and then concentrated. The residue was diluted with ethyl acetate, washed with brine, dried (Na$_2$SO$_4$) and concentrated. The residue was purified by column chromatography on silica gel with hexane/ethyl acetate (95:5) to give the aldehyde 7 (529 mg, 83% yield) as an oil:

$^1$H NMR (400 MHz, CDCl$_3$+TMS) δ 9.60 (1H, d, J=3.1 Hz, CHO), 8.05 (2H, m, o-H$_{Bz}$), 7.57 (1H, m, p-H$_{Bz}$), 7.45 (2H, m, m-H$_{Bz}$), 5.44 (1H, s, 8 α-H), 2.39 (1H, m, 20-H), 2.03 (2H, dm, J=11.5 Hz), 1.15 (3H, d, J=6.9 Hz, 21-H$_3$), 1.10 (3H, s, 18-H$_3$); $^{13}$C NMR (100 MHz) δ 204.78 (d, CHO), 132.78 (d, p-Bz), 130.69 (s, i-Bz), 129.50 (d, o-Bz), 128.38, (d, m-Bz), 71.66 (d, C-8), 51.30 (d), 50.95 (d), 49.20 (d), 42.38 (s, C-13), 39.62 (t), 30.47 (t), 25.99 (t), 22.92 (t), 17.92 (t), 13.90 (q), 13.35 (q); MS (EI) m/z 314 (1, M$^+$), 299 (0.5, M$^+$–Me), 286 (1, M$^+$ —CO), 285 (5, M$^+$ —CHO), 257 (1, M$^+$ —C$_3$H$_5$O), 209 (10, M$^+$–PhCO), 192 (38), 134 (60), 105 (100), 77 (50); exact mass calculated for C$_{20}$H$_{26}$O$_3$ 314.1882. Found 314.1887.

Preparation of (8S,20R)-de-A,B-8-benzoyloxy-20-[(4S)-hydroxy-pent-(1E)-en-yl]pregnane (8)

To a stirred suspension of the phosphonium salt 4 (310 mg, 0.67 mmol) in anhydrous THF (5 mL) butyllithium (1.6 M, 840 μL, 1.34 mmol) was added at –20° C. The solution turned deep orange. After 1 h a precooled (–20° C.) solution of the aldehyde 7 (70 mg, 0.22 mmol) in anhydrous THF (2 mL) was added and the reaction mixture was stirred at –20° C. for 3 h and at room temperature for 18 h. The reaction was quenched with water and the mixture was extracted with ethyl acetate. Combined organic phases were washed with brine, dried (Na$_2$SO$_4$) and evaporated. The residue was chromatographed on silica gel with hexane/ethyl acetate (95:5) to give the product 8 (42 mg, 52% yield):

$[\alpha]_D$+98.7 (c 1.75, CHCl$_3$); $^1$H NMR (400 MHz, CDCl$_3$+TMS) δ 8.05 (2H, m, o-H$_{Bz}$), 7.56 (1H, m, p-H$_{Bz}$), 7.45 (2H, m, m-H$_{Bz}$), 5.41 (1H, s, 8 α-H), 5.40-5.20 (2H, m, 22-H and 23-H), 3.79 (1H, m, 25-H), 1.17 (3H, d, J=6.2 Hz, 27-H$_3$), 1.07 (3H, s, 18-H$_3$), 1.05 (3H, d, J=6.7 Hz, 21-H$_3$); $^{13}$C NMR (100 MHz) δ 166.43 (s, C=O), 140.86 (d, C-22), 132.66 (d, p-C$_{Bz}$), 130.82 (s, i-C$_{Bz}$), 129.50 (d, o-C$_{Bz}$), 128.32 (d, m-C$_{Bz}$), 123.42 (d, C-23), 72.12 (d, C-8), 67.15 (d, C-25), 55.87 (d), 51.63 (d), 42.48 (t), 41.81 (s, C-13), 39.93 (d), 39.79 (t), 30.47 (t), 27.65 (t), 22.59 (t), 22.48 (q, C-27), 20.47 (q, C-21), 17.98 (t), 13.72 (q, C-18); MS (EI) m/z 370 (7, M$^+$), 352 (0.5, M$^+$ —H$_2$O), 326 (2, M$^+$ —C$_2$H$_4$O), 284 (11, M$^+$ —C$_5$H$_{10}$O), 248 (28, M$^+$–PhCOOH), 230 (10), 204 (26), 189 (13), 162 (68), 135 (77), 105 (100); exact mass calculated for C$_{24}$H$_{34}$O$_3$ (M$^+$) 370.2508. Found 370.2491.

Preparation of (8S,20R)-de-A,B-8-benzoyloxy-20-[(4S)-hydroxy-pentyl]pregnane (9)

A solution of the compound 8 (42 mg, 0.11 mmol) in methanol (6 mL) was hydrogenated for 17 h in the presence of 10% palladium on powdered charcoal (7 mg). The reaction mixture was filtered through a bed of Celite with several methanol washes, the filtrate was concentrated and the residue was chromatographed on silica gel with hexane/ethyl acetate (95:5) to give the product 9 (32 mg, 78% yield):

$[\alpha]_D$+72.9 (c 1.4, CHCl$_3$); $^1$H NMR (400 MHz, CDCl$_3$+TMS) δ 8.05 (2H, m, o-H$_{Bz}$), 7.55 (1H, m, p-H$_{Bz}$), 7.44 (2H, m, m-H$_{Bz}$), 5.41 (1H, s, 8 α-H), 3.80 (1H, m, 25-H), 2.04 (2H, m), 1.83 (2H, m), 1.19 (3H, d, J=6.2 Hz, 27-H$_3$), 1.04 (3H, s, 18-H$_3$), 0.95 (3H, d, J=6.5 Hz, 21-H$_3$); $^{13}$C NMR (100 MHz) δ 166.47 (s, C=O), 132.64 (d, p-C$_{Bz}$), 130.86 (s, i-C$_{Bz}$), 129.52 (d, o-C$_{Bz}$), 128.31 (d, m-C$_{Bz}$), 72.23 (d, C-8), 68.12 (d, C-25), 56.32 (d), 51.58 (d), 41.89 (s, C-13), 39.89 (t), 39.72 (t), 35.61 (t), 35.32 (d), 30.53 (t), 27.07 (t), 23.57 (q, C-27), 22.62 (t), 22.12 (t), 18.54 (q, C-21), 18.00 (t), 13.51 (q, C-18); MS (EI) m/z 372 (15, M$^+$), 354 (3, M$^+$ —H$_2$O), 327 (1, M$^+$ —C$_2$H$_5$O), 285 (2, M$^+$ —C$_5$H$_{11}$O), 267 (5, M$^+$–PhCO), 250 (73, M$^+$–PhCOOH), 232 (38), 217 (10), 163 (40), 135 (79), 105 (100); exact mass calculated for C$_{24}$H$_{36}$O$_3$ (M$^+$) 372.2664. Found 372.2671.

Preparation of (8S,20R)-de-A,B-8-benzoyloxy-20-[(4S)-tert-butyldimethylsilyloxy-pentyl]pregnane (10)

tert-Butyldimethylsilyl trifluoromethanesulfonate (37 µL, 42 mg, 0.16 mmol) was added to a solution of the alcohol 9 (32 mg, 0.09 mmol) and 2,6-lutidine (37 µL, 34 mg, 0.32 mmol) in anhydrous methylene chloride (3 mL) at −20° C. The mixture was stirred under argon at 0° C. for 1 h. The reaction was quenched with water and extracted with methylene chloride. The combined organic phases were washed with brine, dried ($Na_2SO_4$) and concentrated under reduced pressure. The residue was chromatographed on silica gel with hexane and hexane/ethyl acetate (97:3) to give the product 10 (42 mg, 96%):

$[\alpha]_D$+58.1 (c 1.6, $CHCl_3$); $^1$H NMR (400 MHz, $CDCl_3$+TMS) δ 8.06 (2H, m, o-$H_{Bz}$), 7.55 (1H, m, p-$H_{Bz}$), 7.44 (2H, m, m-$H_{Bz}$), 5.41 (1H, s, 8 α-H), 3.77 (1H, m, 25-H), 2.04 (2H, m) 1.84 (2H, m), 1.12 (3H, d, J=6.0 Hz, 27$H_3$), 0.93 (3H, d, J=6.5 Hz, 21-$H_3$), 0.89 (9H, s, Si-t-Bu), 0.05 (6H, s, $SiMe_2$); $^{13}$C NMR (100 MHz) δ 166.48 (s, C=O), 132.64 (d, p-$C_{Bz}$), 130.92 (s, i-$C_{Bz}$), 129.55 (d, o-$C_{Bz}$), 128.32 (d, m-$C_{Bz}$), 72.27 (d, C-8), 68.67 (d, C-25), 56.50 (d), 51.62 (d), 41.92 (s, C-13), 40.17 (t), 39.94 (t), 35.75 (t), 35.38 (d), 30.56 (t), 27.10 (t), 25.91 (q, $SiMe_3$), 23.89 (q, C-27), 22.65 (t), 22.20 (t), 18.53 (q, C-21), 18.16 (s, $SiCMe_3$), 18.04 (t), 13.54 (q, C-18), −4.36 (q, SiMe), −4.67 (q, SiMe); MS (EI) m/z 486 (1, $M^+$), 471 (1, $M^+$ —$CH_3$), 307 (8, $M^+$ -PhCOOH—$C_4H_9$), 233 (69, $M^+$–PhCOOH-t-$BuMe_2SiO$), 197 (71), 179 (95), 163 (78), 135 (72), 105 (100); exact mass calculated for $C_{19}H_{35}OSi$ ($M^+$-PhCOOH—$C_4H_9$) 307.2457. Found 307.2453.

Preparation of (8S,20R)-de-A,B-20-[(4S)-tert-butyldimethylsilyloxy-pentyl]pregnan-8-ol (11)

A solution of sodium hydroxide in ethanol (2.5M, 2 mL) was added to a stirred solution of the benzoate 10 (42 mg, 86 µmol) in anhydrous ethanol (10 mL) and the reaction mixture was refluxed for 18 h. The mixture was cooled to room temperature, neutralized with 5% aq. HCl and extracted with dichloromethane. Combined organic phases were washed with saturated aq. $NaHCO_3$, dried ($Na_2SO_4$) and evaporated. The residue was chromatographed on silica gel with hexane/ethyl acetate (95:5) to give the alcohol 11 (24 mg, 73% yield):

$[\alpha]_D$+37.3 (c 1.0, $CHCl_3$); $^1$H NMR (400 MHz, $CDCl_3$+TMS) δ 4.07 (1H, d, J=1.9 Hz, 8 α-H), 3.77 (1H, m, 25-H), 2.00 (1H, m), 1.82 (3H, m), 1.11 (3H, d, J=6.1 Hz, 27-$H_3$), 0.93 (3H, s, 18-$H_3$), 0.89 (3H, d, 21-$H_3$) covered by 0.89 (9H, s, Si-t-Bu), 0.05 (6H, s, $SiMe_2$); $^{13}$C NMR (100 MHz) δ 69.44 (d, C-8), 68.69 (d, C-25), 56.72 (d), 52.60 (d), 41.83 (s, C-13), 40.38 (t), 40.21 (t), 35.80 (t), 35.24 (d), 33.57 (t), 27.16 (t), 25.91 (q, $SiMe_3$), 23.86 (q, C-27), 22.51 (t), 22.21 (t), 18.48 (q, C-21), 18.16 (s, $SiCMe_3$), 17.43 (t), 13.51 (q, C-18), −4.38 (q, SiMe), −4.68 (q, SiMe); MS (EI) m/z 382 (2, $M^+$), 367 (3, $M^+$ —$CH_3$), 325 (9, $M^+$ —$C_4H_9$), 307 (4, $M^+$ —$C_4H_9$—$H_2O$), 233 (61), 191 (45), 177 (75), 159 (70), 135 (84), 123 (85), 109 (96), 97(100); exact mass calculated for $C_{19}H_{37}O_2Si$ ($M^+$ —$C_4H_9$) 325.2563. Found 325.2575.

Preparation of (20R)-de-A,B-20-[(4S)-tert-butyldimethylsilyloxy-pentyl]pregnan-8-one (12)

Pyridinium dichromate (118 mg, 315 µmol) was added to a solution of the alcohol 11 (24 mg, 63 µmol) and pyridinium p-toluenesulfonate (3 mg, 12 µmol) in anhydrous methylene chloride (5 mL). The resulting suspension was stirred at room temperature for 3 h. The reaction mixture was filtered through a Waters silica Sep-Pak cartridge (5 g) that was further washed with hexane/ethyl acetate (8:2). After removal of solvents the ketone 12 (18 mg, 75% yield) was obtained as a colorless oil:

$[\alpha]_D$+11.9 (c 0.9, $CHCl_3$); $^1$H NMR (400 MHz, $CDCl_3$+TMS) δ 3.77 (1H, m, 25-H), 2.44 (1H, dd, J=11.5, 7.6 Hz), 1.11 (3H, d, J=6.1 Hz, 27-$H_3$), 0.94 (3H, d, J=5.9 Hz, 21-$H_3$), 0.88 (9H, s, Si-t-Bu), 0.63 (3H, s, 18-$H_3$), 0.04 (6H, s, $SiMe_2$); $^{13}$C NMR (100 MHz) δ 212.18 (s), 68.62 (d, C-25), 62.00 (d), 56.73 (d), 49.93 (s, C-13), 40.97 (t), 40.10 (t), 38.98 (t), 35.80 (t), 35.46 (d), 27.51 (t), 25.90 (q, $SiMe_3$), 24.07 (t), 23.87 (q, C-27), 22.17 (t), 19.06 (t), 18.65 (q, C-21), 18.16 (s, $SiCMe_3$), 12.47 (q, C-18), −4.36 (q, SiMe), −4.69 (q, SiMe); MS (EI) m/z no $M^+$, 379 (1, $M^+$—H), 365 (4, $M^+$ —$CH_3$), 323 (48, $M^+$ —$C_4H_9$), 281 (34), 250 (39), 231 (56), 207 (41), 189 (32), 159 (62), 125 (70), 75 (100); exact mass calculated for $C_{19}H_{35}O_2Si$ ($M^+$ —$C_4H_9$) 323.2406. Found 323.2415.

Preparation of (20R,25S)-2-Methylene-19,26-dinor-1α-dihydroxyvitamin $D_3$ (15)

To a solution of phosphine oxide 13 (73 mg, 125 µmol) in anhydrous THF (400 µL) at −20° C. was slowly added PhLi (1.8 M in di-n-butylether, 85 µL, 153 µmol) under argon with stirring. The solution turned deep orange. After 30 min the mixture was cooled to −78° C. and a precooled (−78° C.) solution of ketone 12 (18 mg, 47 µmol) in anhydrous THF (200+100 µL) was slowly added. The mixture was stirred under argon at −78° C. for 3 h and at 0° C. for 18 h. Ethyl acetate was added, and the organic phase was washed with brine, dried ($Na_2SO_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 14 (25 mg, 71% yield). Then the Sep-Pak was washed with ethyl acetate to recover diphenylphosphine oxide 13 (43 mg). For analytical purpose a sample of the protected vitamin 14 was further purified by HPLC (9.4×250 mm Zorbax Sil column, 4 mL/min, hexane/2-propanol (99.9:0.1) solvent system, $R_t$=3.77 min):

UV (in hexane) $\lambda_{max}$ 263.1, 253.2, 244.3 nm; $^1$H NMR (400 MHz, $CDCl_3$) δ 6.22 and 5.84 (each 1H, each d, J=11.2 Hz, 6- and 7-H), 4.97 and 4.92 (each 1H, each s, =$CH_2$), 4.43 (2H, m, 1β- and 3 α-H), 3.78 (1H, m, 25-H), 2.82 (1H, dm, J=11.8 Hz, 9β-H), 2.52 (1H, dd, J=13.1, 5.9 Hz, 10 α-H), 2.47 (1H, dd, J=12.6, 4.3 Hz, 4 α-H), 2.33 (1H, dd, J=13.1, 2.3 Hz, 10β-H), 2.18 (1H, dd, J=12.6, 8.7 Hz, 4β-H), 2.00 (2H, m), 1.12 (3H, d, J=6.0 Hz, 27-$H_3$), 0.92 (3H, d, J=6.4 Hz, 21-$H_3$), 0.898 (9H, s, Si-t-Bu), 0.894 (9H, s, Si-t-Bu), 0.867 (9H, s, Si-t-Bu), 0.546 (3H, s, 18-$H_3$), 0.082 (3H, s, SiMe), 0.068 (3H, s, SiMe), 0.054 (9H, s, 3×SiMe), 0.028 (3H, s, SiMe); $^{13}$C NMR (100 MHz) δ 152.99 (s, C-2), 141.27 (s, C-8), 132.69 (s, C-5), 122.43 (d, C-6), 116.09 (d, C-7), 106.25 (t, =$CH_2$), 72.54 and 71.63 (each d, C-1 and C-3), 68.73 (d, C-25), 56.63 (d), 56.29 (d), 47.61 (t), 45.67 (s, C-13), 40.61 (t), 40.24 (t), 38.55 (t), 36.13 (d), 35.98 (t), 28.76 (t), 27.73 (t), 25.93 (q, $SiMe_3$), 25.85 (q, $SiMe_3$) 25.78 (q, $SiMe_3$), 23.89 (q, C-27), 23.45 (t), 22.33 (t), 22.22 (t), 18.77 (q, C-21), 18.25 (s, $SiCMe_3$), 18.17 (s, 2×$SiCMe_3$), 12.06 (q, C-18), −4.37 (q, SiMe), −4.66 (q, SiMe), −4.86 (q, 3×SiMe), −5.09 (q, SiMe); exact mass calculated for $C_{44}H_{84}O_3Si_3Na$ ($MNa^+$) 767.5626. Found 767.5646.

The protected vitamin 14 (25 mg, 34 µmol) was dissolved in THF (2 mL) and acetonitrile (2 mL). A solution of aq. 48% HF in acetonitrile (1:9 ratio, 2 mL) was added at 0° C. and the resulting mixture was stirred at room temperature for 8 h.

Saturated aq. NaHCO$_3$ solution was added and the reaction mixture was extracted with ethyl acetate. The combined organic phases were washed with brine, dried (Na$_2$SO$_4$) and concentrated under reduced pressure. The residue was diluted with 2 mL of hexane/ethyl acetate (8:2) and applied on a Waters silica Sep-Pak cartridge (2 g). An elution with hexane/ethyl acetate (8:2) and later with ethyl acetate gave the crude product 15 (15 mg). The vitamin 15 was further purified by straight phase HPLC [9.4×250 mm Zorbax Sil column, 4 mL/min, hexane/2-propanol (85:15) solvent system, R$_f$=9.31 min.]and by reverse phase HPLC [9.4×250 mm Zorbax Eclipse XDB-C18 column, 3 mL/min, methanol/water (85:15) solvent system, R$_f$=10.16 min.]to give a colorless oil (12.6 mg, 92% yield):

UV (in EtOH) $\lambda_{max}$ 262.1, 252.6, 244.1 nm; $^1$H NMR (600 MHz, CDCl$_3$) δ 6.35 and 5.88 (1H and 1H, each d, J=11.2 Hz, 6- and 7-H), 5.10 and 5.08 (each 1H, each s, =CH$_2$), 4.47 (2H, m, 1β- and 3 α-H), 3.80 (1H, m, 25-H), 2.83 (1H, dd, J=13.3, 4.5 Hz, 10β-H), 2.81 (1H, br d, J=13.2 Hz, 9β-H), 2.56 (1H, dd, J=13.4, 3.7 Hz, 4 α-H), 2.32 (1H, dd, J=13.4, 6.1 Hz, 4 β-H), 2.29 (1H, dd, J=13.3, 8.3 Hz, 10 α-H), 1.19 (3H, d, J=6.2 Hz, 27-H$_3$), 0.93 (3H, d, J=6.4 Hz, 21-H$_3$), 0.546 (3H, s, 18-H$_3$); $^{13}$C NMR (100 MHz) δ 151.97 (s, C-2), 143.39 (s, C-8), 130.42 (s, C-5), 124.20 (d, C-6), 115.28 (d, C-7), 107.70 (t, =CH$_2$), 71.79 and 70.62 (each d, C-1 and C-3), 68.18 (d, C-25), 56.43 (d), 56.30 (d), 45.76 (t), 45.76 (s, C-13), 40.42 (t), 39.75 (t), 38.13 (t), 36.02 (d), 35.80 (t), 28.94 (t), 27.63 (t), 23.54 (q, C-27), 23.48 (t), 22.26 (t), 22.17 (t), 18.78 (q, C-21), 12.06 (q, C-18); MS (EI) m/z 402 (35, M$^+$), 384 (2, M$^+$ —H$_2$O), 369 (2, M$^+$-H$_2$O—CH$_3$), 329 (65, M$^+$ —C$_4$H$_9$O), 287 (13, M$^+$ —C$_7$H$_{15}$O), 257 (100), 229(17), 159 (31), 145 (46), 115 (65), 91 (96); exact mass calculated for C$_{26}$H$_{42}$O$_3$ (M$^+$) 402.3134. Found 402.3129.

EXAMPLE II

Biological Activity (A) Vitamin D Receptor Binding
Test Material
Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of <10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

(B) HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

(C) In vitro Transcription Assay

Transcription activity was measured in ROS 17/2.8 (bone) cells that were stably transfected with a 24-hdyroxylase (24Ohase) gene promoter upstream of a luciferase reporter gene (Arbour et al., 1998). Cells were given a range of doses. Sixteen hours after dosing the cells were harvested and luciferase activities were measured using a luminometer. (RLU=relative luciferase units)

(D) Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

(E) PTH Suppression and Hypercalcemia
Species

Adult, female Sprague-Dawley rats are obtained from Harlan (Madison, Wis.).

Animal Husbandry

Upon receipt, the animals are identified by individual tail marks. Animals may then be housed in suspended, stainless steel, wire-bottom cages. Each cage may contain one animal. The animal rooms are maintained at a temperature of 68 to 72° F. and a relative humidity of 25 to 75%. The holding rooms are set to provide 12 hours of light per day. Water and a purified rodent diet (Suda et al., Purified Rodent Diet-Diet 11) containing 0.47% and 0.3% phosphorus and fat soluble vitamins A, D, E and K are provided ad libitum Treatment Groups Animals are randomly assigned to treatment groups (5 animals/group). All doses are administered intraperitoneally in 100 microliters of propylene glycol. Four to seven consecutive doses are given approximately 24 hours apart. Dosing is initiated after the animals have been allowed to acclimate for at least one week.

Dose Preparation

Control Material

A. Negative Control Material

The negative control material is prepared by volumetrically measuring ethanol (<5%) and propylene glycol, mixing, and then placing in storage at 2 to 8° C.

B. Positive Control Material $1,25(OH)_2D_3$ is prepared by determining the concentration of an ethanol stock solution using UV spectrophotometry (extinction coefficient=18,200; $\lambda_{max}$=265 nm). The required amount of $1,25(OH)_2D_3$ is volumetrically measured into propylene glycol so that there was less than 5% ethanol in the final solution. The solution is mixed and then stored at 2 to 8° C.

Test Material

The analogs are prepared by first determining the concentration of an ethanol stock solution using UV spectrophotometry (extinction coefficient=42,000; $\lambda_{max}$=252 nm). The analog solutions are then volumetrically added to propylene glycol so that there was less than 5% ethanol in the final solution. The solution is mixed and stored at 2 to 8° C.

Dose Administration Method

Both control and test articles are administered by intraperitoneal injection in 100 microliters for 4-7 consecutive days spaced approximately 24 hours apart. $1,25(OH)_2D_3$ is given for 4 consecutive days, whereas, the test drugs are given for 7 consecutive days.

Serum PTH Levels

Twenty-four hours after the final dose, blood is collected from the tail artery and the concentration of bioactive serum PTH is measured using the rat BioActive Intact PTH ELISA Kit from Immutopics, Inc. (San Clemente, Calif.).

Serum Calcium Analysis

Twenty-four hours after the final dose, approximately 1 ml of blood is collected from the tail artery of each experimental animal. The blood is allowed to coagulate at room temperature and then centrifuged at 3000×g for 15 minutes. The serum is transferred to a polypropylene tube and stored frozen at −20° C. The level of calcium is determined by diluting the serum into 0.1% lanthum chloride and measuring the absorbance on an atomic absorption spectrophotometer (Perkin Elmer Model 3110, Shelton, Conn.).

Figure 2:
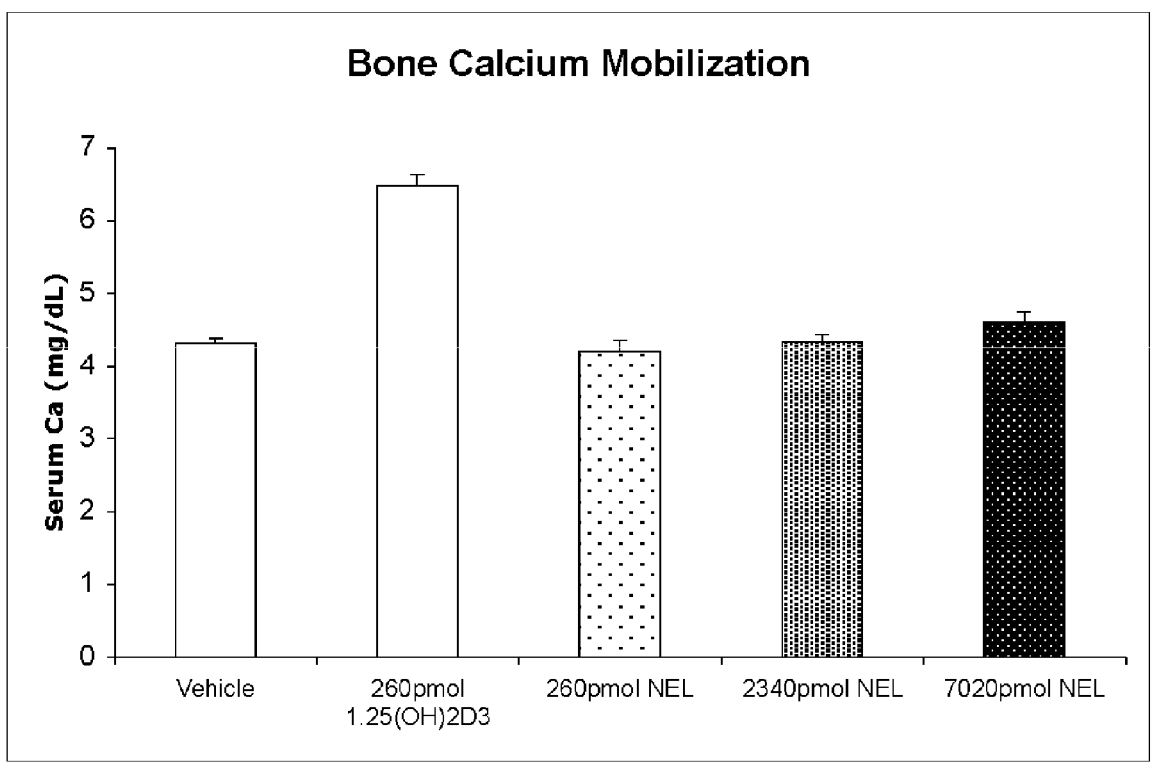
Figure 3:
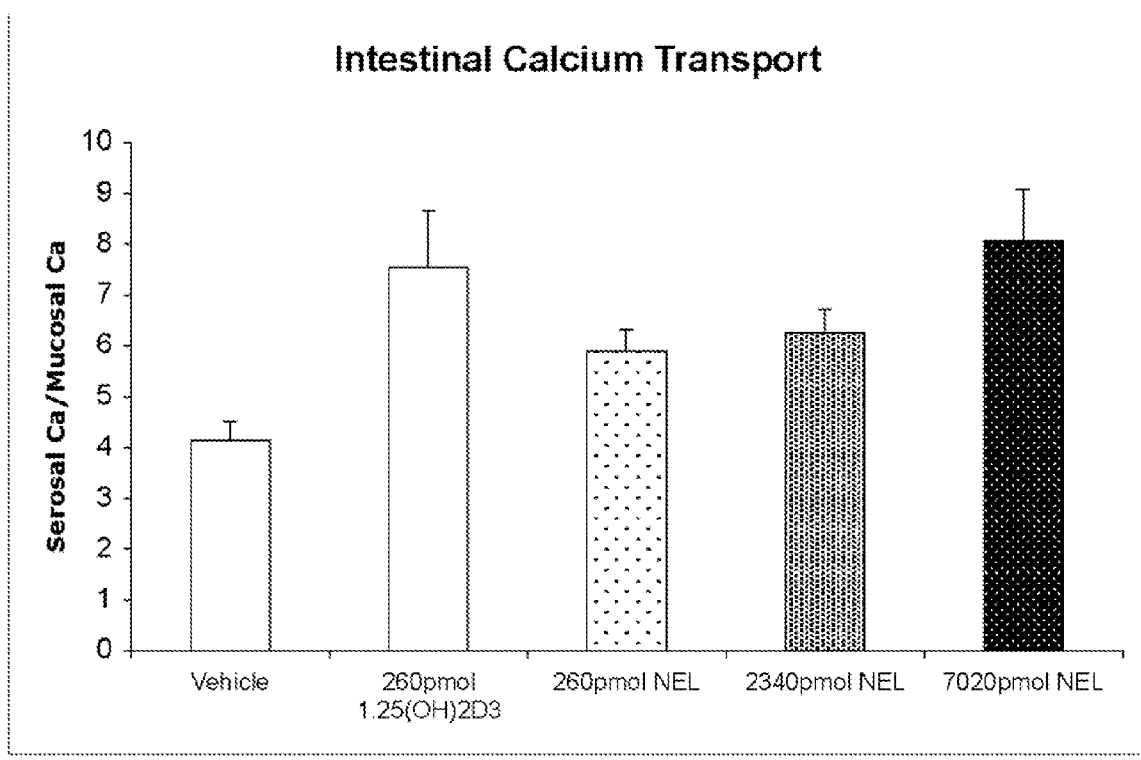
Figure 4:
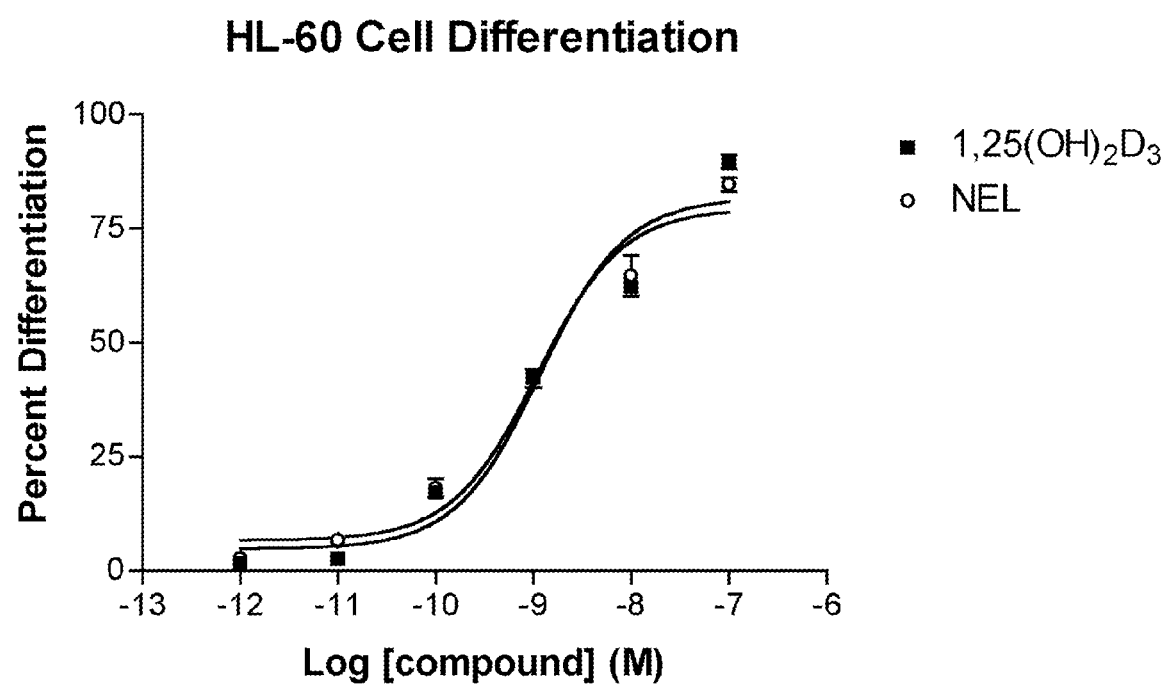
Figure 5:
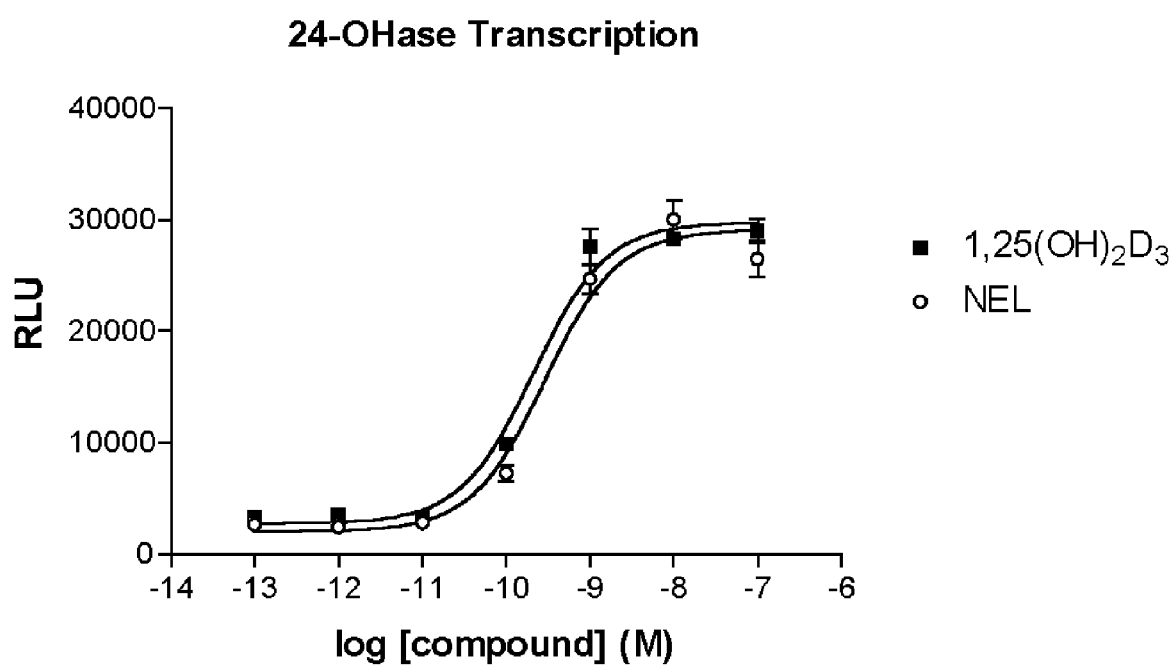

(20R, 25S)-2-Methylene-19,26-dinor-1α,25-dihydroxyvitamin D3 (NEL) binds to the recombinant vitamin D receptor, but is somewhat more active than is 1α,25-dihydroxyvitamin $D_3$ in this respect (see FIG. 1). Additionally, it is equally active in stimulating transcription of a reporter gene stably transfected in Ros17/2.8 (bone) cells, indicating a greater biological activity as 1α,25-dihydroxyvitamin $D_3$ (see FIG. 5). It is also equally active as 1α,25-dihydroxyvitamin $D_3$ in inducing differentiation of HL-60 cells (see FIG. 4). It has limited calcemic activity when measured either by intestinal calcium transport or bone calcium mobilization at equimolar quantities or even when given at 27 times the dose of 1α,25-dihydroxyvitamin $D_3$ (see FIGS. 2 and 3). Accordingly, NEL is expected to possess significant activity in suppressing parathyroid hormone levels in normal rats.

Similarly, other similar compounds of the present invention as shown in formula IA, IB, are expected to bind to the vitamin D receptor, stimulate transcription of a reporter gene stably transfected in Ros17/2.8 (bone) cells, induce differentiation of HL-60 cells, have limited calcemic activity when measured either by intestinal calcium transport or bone calcium mobilization than 1α,25-dihydroxyvitamin $D_3$ and possess significant activity in suppressing parathyroid hormone levels in normal rats.

Accordingly, this compound NEL and other compounds described in the invention find their uses in the treatment of autoimmune diseases such as multiple sclerosis, type I diabetes, rheumatoid arthritis, lupus, and other similar degenerative diseases. These compositions also have significant utility in treating malignant growth such as colorectal, breast and prostate cancers. The suitability for the compositions disclosed herein for the uses described above is evident from the absence of the increase in serum calcium concentrations (see FIG. 3). These compounds also show promise in treating secondary hyperparathyroidism found in patients who have lost kidney function such as those on hemodialysis or peritoneal dialysis.

In one embodiment, the compounds of formula IA or IB is used in a pharmaceutical composition. For example, each ml of the pharmaceutical composition may comprise 5 μg of the compound, 30% (v/v) propylene glycol and 20% (v/v) alcohol.

The compounds of the invention are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and or reducing body fat in animal subject includes administering to the animal subject, an effective amount of the compound or a pharmaceutical composition that includes the compound. Administration of the compound or the pharmaceutical composition to the subject inhibits adipocyte differentiation, inhibits gene transcription, and/or reduces body fat in the animal subject. In addition, it should be appreciated that the compounds described herein are useful for the cosmetic treatment of overweight. In such instances, the compositions are administered in any way desirable at an effective amount to realize the cosmetic goal.

For treatment purposes, the compounds defined by formula I, i.e., formula IA, and formula IB, and formula II, i.e., formula IIA and IIB is formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, antioxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds are administered orally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 µg to about 1 mg per day of the compound are appropriate for treatment purposes. In some such embodiments an appropriate and effective dose may range from 0.01 µg to 1 mg per day of the compound. In other such embodiments an appropriate and effective dose may range from 0.1 µg to 500 µg per day of the compound. Such doses will be adjusted according to the type of disease or condition to be treated, the severity of the disease or condition, and the response of the subject as is well understood in the art. The compound is suitably administered alone, or together with another active vitamin D compound.

In one embodiment, the compound of formula IIA is used in a pharmaceutical composition. For example, each ml of the pharmaceutical composition may comprise 5 µg of the compound, 30% (v/v) propylene glycol and 20% (v/v) alcohol.

Compositions for use in the invention include an effective amount of (20R, 25S)-2-Methylene-19,26-dinor-1α,25-dihydroxyvitamin D3 or (20S, 25S)-2-Methylene-19,26-dinor-1α,25-dihydroxyvitamin D3 as the active ingredient, and a suitable carrier. An effective amount of the compound for use in accordance with some embodiments of the invention will generally be a dosage amount such as those described herein, and is administered topically, transdermally, orally, nasally, rectally, or parenterally. In one embodiment, the dosage is administered intraperitoneally.

The compounds of formula IA, IB, IIA or IIB are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compound is formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration is in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration is in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and is prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A compound having the formula IA or IB

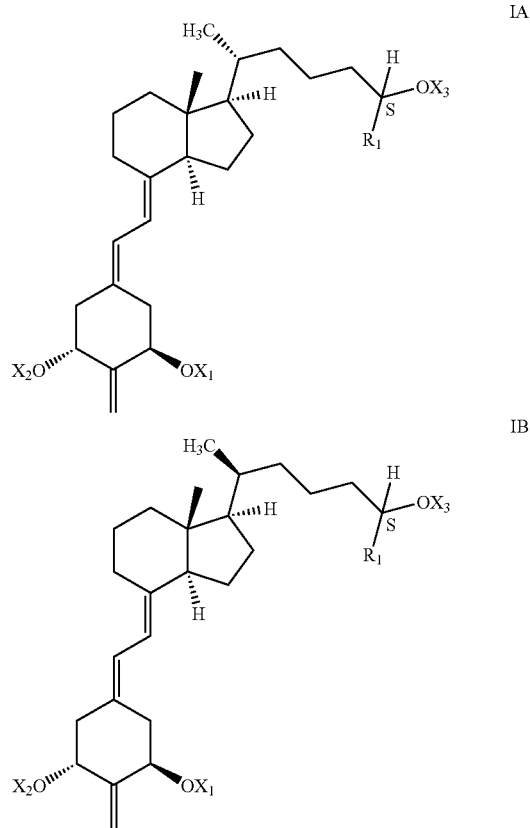

wherein $X_1$, $X_2$ and $X_3$ are independently selected from H and hydroxy protecting groups; and $R_1$ is selected from straight or branched chain alkyl groups having from 1 to 8 carbon atoms; straight or branched chain alkenyl groups having from 2 to 8 carbon atoms; straight or branched chain hydroxy-substituted alkyl groups having from 1 to 8 carbon atoms; straight and branched chain hydroxy-substituted alkenyl groups having from 2 to 8 carbon atoms.

2. The compound of claim 1, wherein $X_1$, $X_2$ and $X_3$ are hydroxy protecting groups.

3. The compound of claim 2, wherein $X_1$, $X_2$ and $X_3$ are t-butyldimethylsilyl groups.

4. The compound of claim 1, wherein $X_1$, $X_2$ and $X_3$ are H and $R_1$ is $CH_3$ and the compound has the formula IIA or IIB

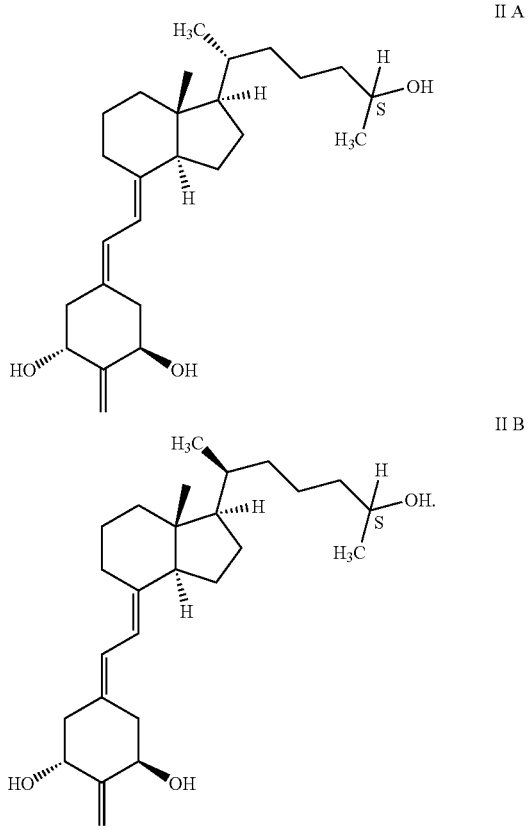

5. A pharmaceutical composition, comprising an effective amount of the compound of claim 1 and a pharmaceutically acceptable carrier.

6. The pharmaceutical composition of claim 5 wherein the effective amount comprises from about 0.01 μg to about 1 mg of the compound per gram of the composition.

7. The pharmaceutical composition of claim 5 wherein the effective amount comprises from about 0.1 μg to about 500 μg of the compound per gram of the composition.

8. A method of treating a subject suffering from a biological condition, comprising administering an effective amount of the compound of claim 1 to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; osteoporosis; vitamin D resistant rickets; or psoriatic arthritis.

9. The method of claim 8, wherein the biological condition is renal osteodystrophy, vitamin D-resistant rickets, osteoporosis or psoriatic arthritis.

10. The method of claim 8, wherein the biological condition is selected from leukemia, colon cancer, breast cancer, or prostate cancer.

11. The method of claim 8, wherein the biological condition is selected from multiple sclerosis, lupus, diabetes mellitus, host versus graft reaction, or rejection of organ transplants.

12. The method of claim 8, wherein the biological condition is selected from rheumatoid arthritis, asthma, or inflammatory bowel diseases selected from celiac disease, ulcerative colitis and Crohn's disease.

13. The method of claim 8, wherein the biological condition is selected from wrinkles, lack of adequate skin firmness, lack of adequate dermal hydration, or insufficient sebum secretion.

14. The method of claim 8, wherein the compound is administered orally, parenterally, transdermally or topically to the subject.

15. The method of claim 8, wherein the compound is administered intraperitoneally.

16. The method of claim 8, wherein the compound is administered in a dosage of from 0.01 μg per day to 1 mg per day.

17. The compound having the formula IIA

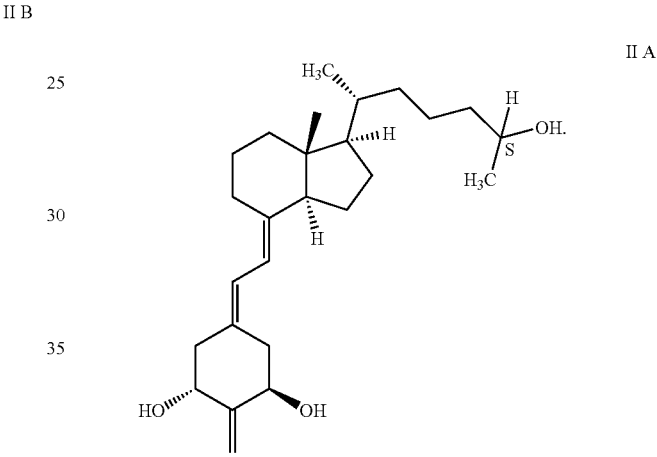

18. A pharmaceutical composition, comprising an effective amount of the compound of claim 17 and a pharmaceutically acceptable carrier.

19. The compound having the formula IIB

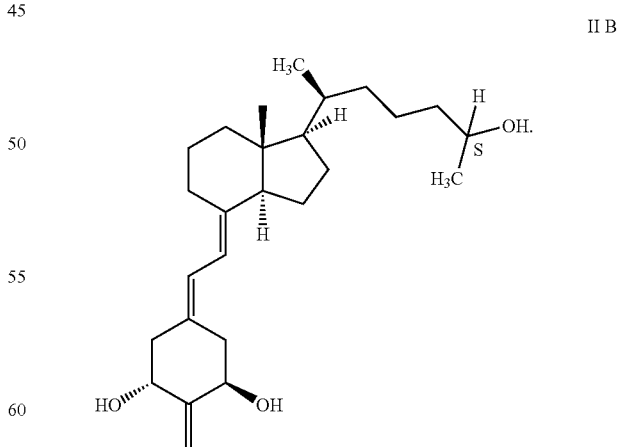

20. A pharmaceutical composition, comprising an effective amount of the compound of claim 19 and a pharmaceutically acceptable carrier.

* * * * *